(12) United States Patent
Bacher et al.

(10) Patent No.: US 7,288,367 B2
(45) Date of Patent: Oct. 30, 2007

(54) NON-MEVALONATE ISOPRENOID PATHWAY

(76) Inventors: Adelbert Bacher, Königsbergerstr. 74, 85748 München/Garching (DE); Meinhart H. Zenk, Carl-von-Ossietzky-Strasse 12/I, 06114 Halle/Saalem (DE); Petra Adam, Engelhofstrasse 6, 85386 Dietersheim (DE); Wolfgang Eisenreich, Römerhofweg 51a, 85748, Garching (DE); Monika Fellermeier, Eichenweg 6, 83556 Griesstätt (DE); Stefan Hecht, Engelhofstrasse 6, 85386 Dietersheim (DE); Felix Rohdich, Moosburger Strasse 16, 85406, Zolling (DE); Christoph A. Schuhr, Bertoldstrasse 19, 51065 Köln (DE); Juraithip Wungsintaweekul, Reischlsweg 8A, 80939, München (DE)

( * ) Notice: Subject to any disclaimer, the term of this patent is extended or adjusted under 35 U.S.C. 154(b) by 82 days.

(21) Appl. No.: 10/296,416

(22) PCT Filed: Jun. 1, 2001

(86) PCT No.: PCT/EP01/06255

§ 371 (c)(1),
(2), (4) Date: Jul. 8, 2003

(87) PCT Pub. No.: WO01/94561

PCT Pub. Date: Dec. 13, 2001

(65) Prior Publication Data

US 2004/0072142 A1    Apr. 15, 2004

(30) Foreign Application Priority Data

Jun. 5, 2000    (DE) ................. 100 27 821

(51) Int. Cl.
*C12Q 1/00*    (2006.01)
(52) U.S. Cl. ........................................ 435/4
(58) Field of Classification Search .................. 435/4; 558/73; 530/370
See application file for complete search history.

(56) References Cited

U.S. PATENT DOCUMENTS

| | | | | |
|---|---|---|---|---|
| 5,824,873 | A | 10/1998 | Grierson et al. | 800/205 |
| 5,885,782 | A | 3/1999 | Edwards | 435/7.1 |
| 2004/0176570 | A1* | 9/2004 | Bacher et al. | 530/350 |
| 2004/0226502 | A1 | 11/2004 | Bacher et al. | 117/2 |

FOREIGN PATENT DOCUMENTS

| | | | |
|---|---|---|---|
| CA | 2374608 | A1 * | 11/2000 |
| DE | 298 00 547 | U1 | 4/1999 |
| EP | 0 154 204 | A2 | 9/1985 |
| EP | 0841394 | | 5/1998 |
| WO | WO98/42875 | | 10/1998 |
| WO | WO 99/11757 | | 3/1999 |
| WO | WO99/52938 | | 10/1999 |
| WO | WO99/58649 | | 11/1999 |
| WO | WO 00/17233 | | 3/2000 |
| WO | 00/36138 | A1 * | 6/2000 |
| WO | WO 00/72022 | | 11/2000 |
| WO | WO 01/11055 | | 2/2001 |
| WO | WO 01/85950 | | 11/2001 |
| WO | WO 01/94561 | A2 | 12/2001 |
| WO | WO 02/12478 | A2 | 2/2002 |
| WO | WO 02/083720 | A2 | 10/2002 |
| WO | WO 02/092800 | A2 | 11/2002 |
| WO | WO 02/102991 | | 12/2002 |

OTHER PUBLICATIONS

Tohihi et al., 1990, CAS:112:231404.*
Tetrahedron Letters vol. 39 (Oct. 1998) pp. 7913-7916.*
Chemistry and Biology vol. 5 (1998) pp. R221-R233.*
Lichtenthaler, Biochemical Society Transactions 28:785-789 (2000).*
Eisenreich et al., Cellular and Molecular Life Sciences 61:1401-1426 (2004).*
Rohdich et al., Bioorganic Chemistry 32:292-308 (2004).*
Rohdich et al., Biochemical Society Transactions 33:785-791 (2005).*
Baker et al. 1992. Sequence and Characterization of the *gcpE* Gene of *Escherichia coli*. FEMS Microbiology Letters 94:175-180.
Campos et al. 2001. Identification of *gcpE* as a Novel Gene of the 2-C-methyl-D-erythritol 4-phosphate Pathway for Isoprenoid Biosynthesis in *Escherichia coli*. FEBS Letters 488:170-173.

(Continued)

*Primary Examiner*—Mark L. Shibuya
*Assistant Examiner*—J. S. Lundgren
(74) *Attorney, Agent, or Firm*—Myers Bigel Sibley & Sajovec

(57) ABSTRACT

The present invention is directed to enzymes and intermediates of the non-mevalonate isoprenoid pathway downstream of 2C-methyl-D-erythritol 2,4-cyclopyrophosphate and upstream of isopentenyl pyrophosphate or dimethylallyl pyrophosphate. These are used as a basis for a screening method for inhibitors of these enzymes, and a method for identifying inhibitor-resistant variants thereof. Further disclosures refer to DNA coding for said enzymes and for inhibitor-resistant variants thereof, vectors containing said DNA, cells containing said vector, and plant seeds comprising cells containing said vector. This invention is useful for the inhibition of the biosynthesis of isoprenoids in plants, bacteria and protozoa, for confering herbicide-resistance to plants, as well as for weed control in agriculture using a crop containing a herbicide-resistant gene and an effective amount of a suitable herbicide.

6 Claims, 3 Drawing Sheets

OTHER PUBLICATIONS

Cunningham et al. 2000. Evidence of a Role for LytB in the Nonmevalonate Pathway of Isoprenoid Biosynthesis. *Journal of Bacteriology* 182:5841-5848.

Gustafson et al. 1993. Identification of the *Escherichia coli lytB* Gene, Which is Involved in Penicillin Tolerance and Control of the Stringent Response. *Journal of Bacteriology* 175:1203-1205.

Hecht et al. 2001. Studies on the Nonmevalonate Pathway to Terpenes: The Role of the GcpE (IspG) Protein. *PNAS* 98:14837-14842.

Herz et al. 2000. Biosynthesis of Terpenoids: YgbB Protein Converts 4-diphosphocytidyl-2C-methyl-D-erythritol 2-phosphate to 2C-methyl-D-erythritol 2,4-cyclodiphosphate. *PNAS* 97:2486-2490.

Lüttgen et al. 2000. Biosynthesis of Terpenoids: YchB Protein of *Escherichia coli* Phosphorylates the 2-hydroxy Group of 4-diphosphocytidyl-2C-methyl-D-erythritol. *PNAS* 97:1062-1067.

Ostrovsky et al. 1993. Bacterial Oxidative-Stress Substance is 2-C-methyl-D-erythritol 2,4-cyclopyrophosphate. *Biochemical Journal* 295:901-902.

Potter et al. 1998. Occurrence of Homologs of the *Escherichia coli lytB* Gene in Gram-Negative Bacterial Species. *Journal of Bacteriology* 180:1959-1961.

Rodriquez-Concepción et al. 2000. Genetic Evidence of Branching in the Isoprenoid Pathway for the Production of Isopentenyl Diphosphate and Dimethylallyl Diphosphate in *Escherichia coli*. *FEBS Letters* 473:328-332.

Rohdich et al. 1999. Cytidine 5'-triphosphate-dependent Biosynthesis of Isoprenoids: YgbP Protein of *Escherichia coli* Catalyzes the Formation of 4-diphosphocytidyl-2-C-methylerythritol. *PNAS* 96:11758-11763.

Rohdich et al. 2002. Studies of the Nonmevalonate Terpene Biosynthetic Pathway: Metabolic Role of IspH (LytB) Protein. *PNAS* 99:1158-1163.

Rohmer. 1998. Isoprenoid Biosynthesis via the Mevalonate-independent Route, a Novel Target for Antibacterial Drugs? *Progress in Drug Research* 50:135-154.

International Search Report for International Application Serial No. PCT/EP01/06255, mailed Apr. 2, 2002.

Rohdich et al. 1999. Cytidine 5'-triphosphate-dependent Biosynthesis of Isoprenoids: YgbP Protein of *Escherichia coli* Catalyzes the Formation of 4-diphosphocytidyl-2-C-methylerythritol. *PNAS* 96:11758-11763.

Gabrielsen et al., (2004), "Hexameric Assembly of the Bifunctional Methylerythritol 2,4-Cyclodiphosphate Synthase and Protein-Protein Associations in the Deoxy-xylulose-dependent Pathway of Isoprenoid Precursor Biosynthesis", The Journal of Biological Chemistry, 279:52753-52761.

Blattner et al. (1997) "The Complete Genome Sequence of *Escherichia coli* K12 "*Science* 277:1453-1462.

Post et al. (1993) "Characterization of the *hemA-prs* region of the *Escherichia coli* and *Salmonella typhimurium* chromosomes: identification of two open reading frames and implications for *prs* expression " *J. Gen. Microbiol.* 139:259-266.

International Search Report for International Application Serial No. PCT/EP00/07548, mailed Dec. 12, 2000.

Abola et al. (2000) "Automation of X-ray crystallography "*Nature Structural Biology* 7:973-977.

Richard et al. (2002) "Structure and Mechanism of 2-*C*-Methyl-D-erythritol 2,4-Cyclodiphosphate Synthase " *The Journal of Biological Chemistry* 277:8667-8672.

Skelly et al. (1996) "Overexpression, Isolation, and Crystallization of Proteins " *Methods in Molecular Biology* 56:23-53.

Steinbacher et al. (2002) "Structure of 2*C*-Methyl-D-erythritol-2,4-cyclodiphosphate Synthase Involved in Mevalonate-independent Biosynthesis of Isoprenoids" *J. Mol. Biol.* 316:79-88.

Ridley, R.G. (1999) "Planting the seeds of new antimalarial drugs" *Science* 285:1502-1503.

GenBank Accession No. P36663 "2-C-methyl-D-erythritol 2,4-cyclodiphosphate synthase" Jun. 1, 1994.

International Search Report mailed on Jun. 13, 2003 for application No. PCT/EP 02/05238.

Altincicek et al. (2001) "GcpE Is Involved in the 2-*C*-Methyl-D-Erythritol 4-Phosphate Pathway of Isoprenoid Biosynthesis in *Escherichia coli*" *Journal of Bacteriology* 183:2411-2416.

Parker, J. (1992) "E. coli gcpE gene" *EMBL Database* accession No. X64451 1-2.

Nakamura, Y. (1997) "*Arabidopsis thaliana* genomic DNA, chromosome 5, P1 clone" *EMBL Database* accession no AB005246 1-26.

Lichtenthaler, H. K. (2000) "Non-mevalonate isoprenoid biosynthesis: enzymes, genes and inhibitors" *Biochemical Society Transactions* 28:785-789.

Lichtenthaler et al. (2000) "The Non-Mevalonate Isoprenoid Biosynthesis of Plants as a Test System for New Herbicides and Drugs against Pathogenic Bacteria and the Malaria Parasite" *Journal of Biosciences* 55:305-313.

Wolff et al. (2002) "Isoprenoid biosynthesis via the methylerythritol phosphate pathway. (*E*)-4-Hydroxy-3-methylbut-2-enyl diphosphate: chemical synthesis and formation from methylerythritol cyclodiphosphate by a cell-free system from *Escherichia coli*" *Tetrahedron Letters* 43:2555-2559.

International Search Report mailed on Jan. 15, 2003 for application No. PCT/EP 02/04005.

Tagaki et al. "Studies on the nonmevalonate pathway: formation of 2-C-methyl-D-erythritol 2,4-cyclodiphosphate from 2-phospho-4-(cytidine 5'-diphospho)-2-C-methyl-D-erythritol" *Tetrahedron Letters* 41:3395-3398 (2000).

Kuzuyama et al. "Studies on the nonmevalonate pathway: conversion of 4-(cytidine 5'-diphospho)-2-C-methyl-D-erythritol to its 2-phospho derivative by 4-(cytidine 5'-diphospho)-2-C-methyl-D-erythritol kinase" *Tetrahedron Letters* 41:2925-2928 (2000).

Examination Report issued for European Patent Application No. 01 940 547.1-1212 dated Oct. 11, 2006 (8 pages).

Fellermeier. Copy of Ph.D. thesis entitled "Untersuchungen zum alternativen Terpenbiosyntheseweg in Pflanzen" Submitted to the University Library Munich, Ludwig-Maximilians-University, Munich, Germany in Jul., 2000 (345 pages). (German).

Rodich, F. et al., The deoxyxylulose phosphate pathway of isoprenoid biosynthesis: Studies on the mechanisms of the reactions catalyzed by IspG and IspH pretein, Proc. Nat'l. Acad. Sci. USA, 100(4), Feb. 18, 2003, 1586-1591.

Fellermeier. Copy of Ph.D. thesis entitled "Investigations on the Alternative Terpene Biosynthesis Pathway in Plants" Submitted to the University Library Munich, Ludwig-Maximilians-University, Munich, Germany in Jul., 2000 (English translation of introductory pages, reference list, indes, pp. 50-53, 61-63, 128-151, 164-175, 200-207, 313-361).

* cited by examiner

NON-MEVALONATE ISOPRENOID PATHWAY

FIELD OF THE INVENTION

The present invention relates to the non-mevalonate isoprenoid pathway. More particularly, it relates to intermediates downstream from 2C-methyl-D-erythritol 2,4-cyclopyrophosphate and their production and to genes and proteins operative in their biosynthesis; as well as purified isolated DNA coding for said proteins and expression vectors containing a sequence of such DNA as well as recombinant cells containing such vectors. Moreover, the present invention relates to a screening method for detecting inhibitors of enzymatic conversions downstream from 2C-methyl-D-erythritol 2,4-cyclopyrophosphate and to inhibitors, notably herbicides, detectable thereby as well as. compositions and processes for inhibiting the synthesis of isoprenoids and for controlling the growth of organisms, notably plants based on said inhibitors. The invention also relates to the development of inhibitor-resistant plant enzymes and plants, plant tissues, plant seeds and plant cells.

By the classical research of Bloch, Cornforth, Lynen and coworkers, isopentenyl pyrophosphate (IPP) and dimethylallyl pyrophosphate (DMAPP) have been established as key intermediates in the biosynthesis of isoprenoids via mevalonate. It has recently been detected that in most bacteria, in protists like *Plasmodium falciparum* and in the plastids of plants an alternative non-mevalonate pathway is operative. It has so far only been partially explored. It can be conceptualized to consist of three segments:

In a first pathway segment shown in FIG. 1 pyruvate (1) and D-glyceraldehyde 3-phosphate (2) undergo a condensation to 1-deoxy-D-xylulose 5-phosphate (DXP) (3) by 1-deoxy-D-xylulose 5-phosphate synthase. Subsequently, DXP is converted to 2C-methyl-D-erythritol 4-phosphate (4) by a two-step reaction comprising a rearrangement and a reduction by 1-deoxy-D-xylulose 5-phosphate reductoisomerase. This establishes the 5-carbon isoprenoid skeleton.

In the subsequent segment of the non-mevalonate pathway (FIGS. 2 and 3), 2C-methyl-D-erythritol 4-phosphate (4) is first condensed with CTP to 4-diphosphocytidyl-2C-methyl-D-erythritol (5) in the presence of magnesium ions. This intermediate (5) is subsequently condensed with ATP to 4-diphosphocytidyl-2C-methyl-erythritol 2-phosphate (6) by 4-diphosphocytidyl-2C-methyl-D-erythritol kinase in the presence of magnesium ions. The intermediate (6) is subsequently converted into 2C-methyl-D-erythritol 2,4-cyclopyrophosphate (7). These three enzymatic steps form a biosynthetic unit which activates the isoprenoid $C_5$-skeleton for the third pathway segment (Rodich et al. Proc. Natl. Acad. Sci. USA 96, 11758–11763 (1999); Lyttgen et al. Proc. Natl. Acad. Sci. USA 97, 1062–1067 (2000); Herz et al. Proc. Natl. Acad. Sci. USA 97, 2486–2490 (2000)).

The third pathway segment (FIG. 3) is the subject of the present invention. It concerns the reductive conversion of 2C-methyl-D-erythritol 2,4-cyclopyrophosphate into intermediates of the type isopentenyl pyrophosphate (IPP)(compound 8 in FIG. 3) or dimethylallyl pyrophosphate (DMAPP)(compound 9 in FIG. 3). With this segment, the non-mevalonate isoprenoid pathway (a trunk pathway) is completed. IPP and DMAPP subsequently undergo condensation into higher isoprenoids (or terpenoids).

The non-mevalonate isoprenoid pathway is wholly absent in animals. This makes it an ideal target for pesticidal or medical purposes. The idiosyncratic nature of the reactions in this pathway reduces the risk of cross-inhibition with other, notably mammalian enzymes.

SUMMARY OF THE INVENTION

Therefore, it is a first object of the invention to provide a chemical compound which serves as intermediate in the non-mevalonate isoprenoid pathway downstream from 2C-methyl-D-erythritol 2,4-cyclopyrophosphate and upstream from the intermediates of the type IPP or DMAPP. This object has been achieved by the compounds of claims 1 to 5 or by the cell fluid of claims 6 or 7.

It is a second object of the invention to provide a process for converting 2C-methyl-D-erythritol 2,4-cyclopyrophosphate into an intermediate downstream from 2C-methyl-D-erythritol 2,4-cyclopyrophosphate and upstream from the intermediates of the type IPP or DMAPP. This object is achieved by the process according to claims 8 to 10.

It is a third object of the invention to provide a method of screening for inhibitors of an enzyme operative downstream from 2C-methyl-D-erythritol 2,4-cyclopyrophosphate. The object is achieved by the methods of claims 17 to 19.

It is a fourth object of the invention to provide an enzyme in a form that is functional in the non-mevalonate isoprenoid pathway downstream from 2C-methyl-D-erythritol 2,4-cyclopyrophosphate. This object is achieved by the enzyme according to claim 12 or by a protein comprising such enzyme.

It is a further object of the invention to provide a purified, isolated nucleic acid, notably DNA, coding for an enzyme in accordance with claim 12 or a vector or recombinant cell derived therefrom. This object has been achieved by the subject matter of claims 13 to 16.

It is a further object of the invention to provide a method for identifying an inhibitor-resistant variant of one of the above enzymes as well as of nucleic acids and DNA vectors encoding said variants as well as cells and seeds of plants harboring such vector as well as a method for conferring inhibitor-resistance to plants and a corresponding method of weed control. These objects are achieved in accordance with claims 20 to 28.

It is a further object of the invention to provide a novel inhibitor for an above-identified enzyme, compositions containing such inhibitor and methods of in vivo inhibiting the biosynthesis of isoprenoids. These objects are achieved in accordance with claims 29 to 31.

Wherever a phosphorylated compound or carboxylic acid compound is mentioned herein it may exist as a free acid or as a salt with at least one proton replaced by ammonium or a metal ion or an organic cation. The metal ion may preferably be an alkali metal ion or an alkaline earth metal ion. The organic cation may be derived from an amine. It may be a sulphonium ion, a guanidinium ion or a heteroaromatic ion.

DETAILED DESCRIPTION OF THE INVENTION

Figure 1:
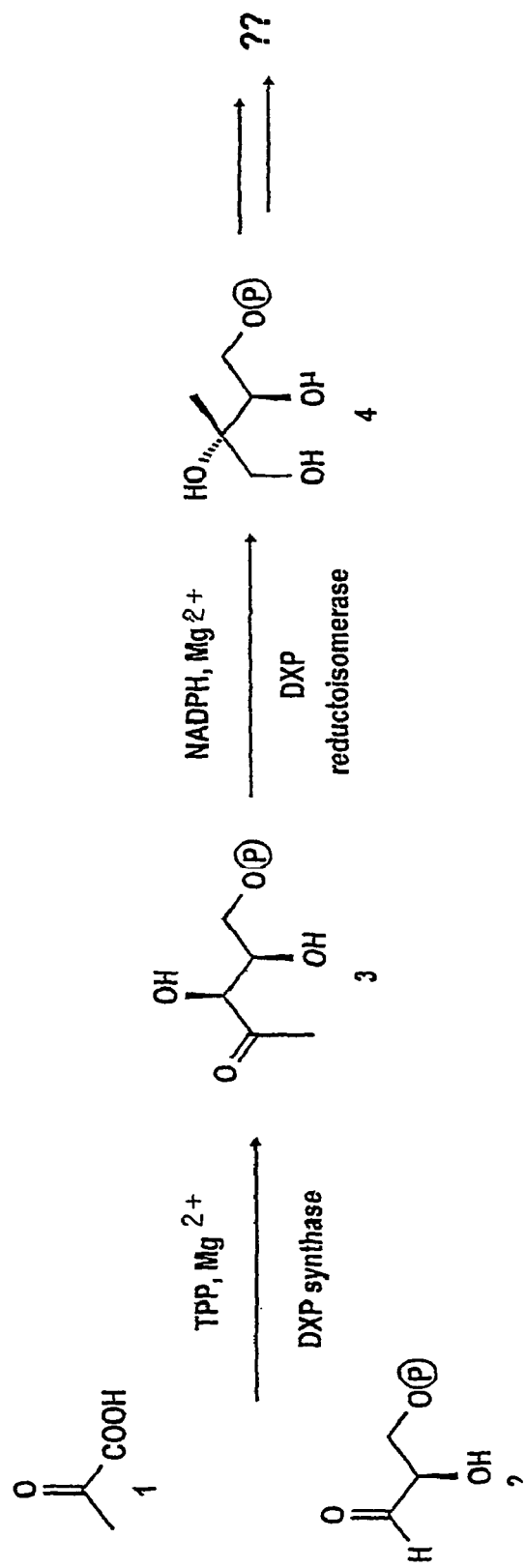
FIG. 1 shows the previously established first pathway segment of the non-mevalonate pathway.
Figure 2:
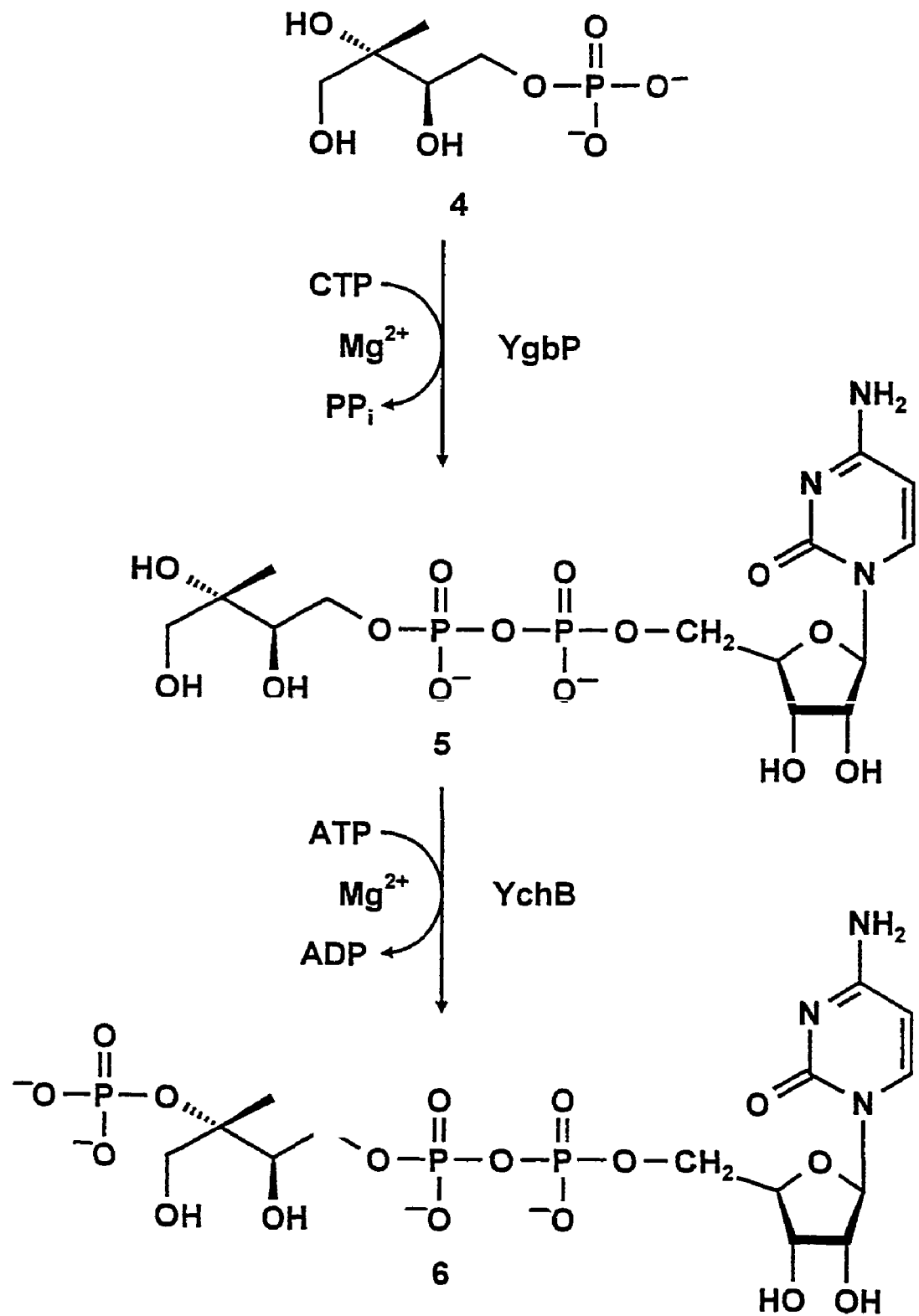
FIGS. 2 and 3 show the previously established second pathway segment of the non-mevalonate pathway.
Figure 3:
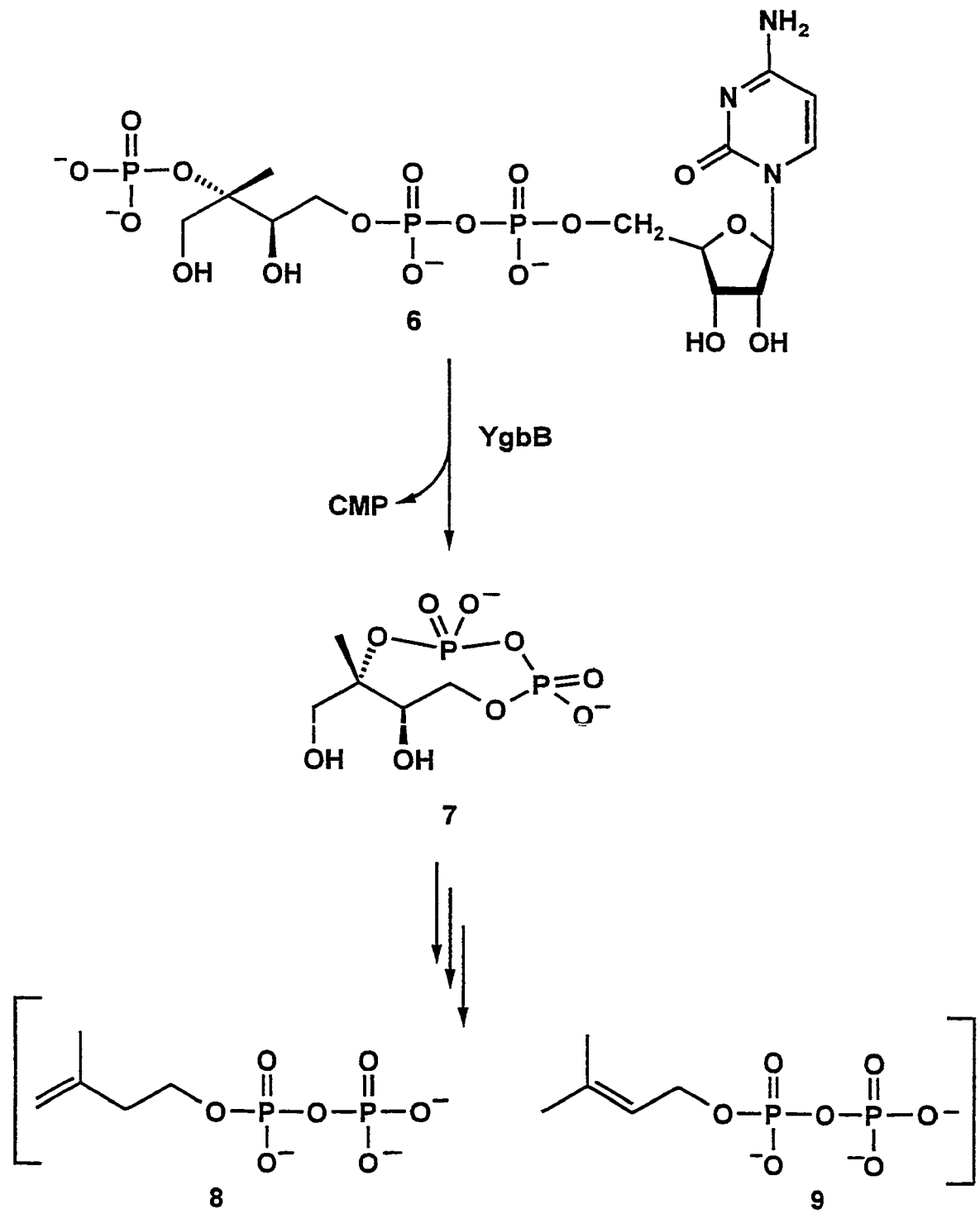

Synthesis of 2C-Methyl-D-erythritol 2,4-Cyclopyrophosphate 2C-methyl-D-erythritol 2,4-cyclopyrophosphate is a key substance for the invention. It may be obtained in the required amounts by a large-scale enzymatic preparation. The immediate starting materials for this preparation are pyruvate and D-glyceraldehyde 3-phosphate. However, it is preferred to use dihydroxyacetone phosphate in conjunction with triosephosphate isomerase under appropriate conditions as a source for D-glyceraldehyde 3-phosphate. Still more advantageous is the use of glucose and ATP in conjunction with the glycolytic enzymes hexokinase, phosphoglucose isomerase, phosphofructokinase, aldolase and triosephosphate isomerase.

For the special case of dihydroxyacetone phosphate, the production of 2C-methyl-D-erythritol 2,4-cyclopyrophosphate may be characterized as follows:

(a) reacting dihydroxyacetone phosphate and sodium pyruvate in the presence of magnesium salt, thiamine pyrophosphate, triose phosphate isomerase and 1-deoxy-D-xylulose 5-phosphate synthase to produce 1-deoxy-D-xylulose 5-phosphate;

(b) reacting the reaction mixture obtained in step (a) with glucose and NADP$^+$ in the presence of an Mg$^{2+}$ or Mn$^{2+}$ salt, glucose dehydrogenase and 1-deoxy-D-xylulose 5-phosphate reductoisomerase to produce 2C-methyl-D-erythritol 4-phosphate;

(c) reacting the reaction mixture obtained in step (b) with cytidyl triphosphate, an enzyme as defined below and a divalent metal salt to produce 4-diphosphocytidyl-2C-methyl-D-erythritol;

(d) reacting the reaction mixture obtained in step (c) with adenosine triphosphate, a divalent metal salt and an enzyme as defined below to produce 4-diphosphocytidyl-2C-methyl-D-erythritol 2-phosphate;

(e) reacting the reaction mixture obtained in step (d) with an enzyme as defined below to produce 2C-methyl-D-erythritol 2,4-cyclopyrophosphate;

(f) isolating the product of step (e).

For step (a) the enzyme 1-deoxy-D-xylulose 5-phosphate synthase is produced in accordance with a previously described method from *Bacillus subtilis* (Williams et al., J. Bacteriol. 146 (3), 1162–1165 (1981)) and as exemplified herein.

Dihydroxyacetone phosphate is produced in accordance with Effenberger et al. (Tetrahedron Lett. 28, 1641–1644 (1987)). For step (b) 1-deoxy-D-xylulose 5-phosphate reductoisomerase is produced in accordance with a previously described method from *E. coli*. For step (c) the enzyme 4-diphosphocytidyl-2C-methyl-D-erythritol synthase is required. This enzyme is obtained by expressing the gene ygbP of *E. coli* as described herein. For step (d) the enzyme 4-diphosphocytidyl-2C-methyl-D-erythritol kinase is required. This enzyme is obtained by expressing the gene ychB of *E. coli* as described herein.

For step (e) the enzyme 2C-methyl-D-erythritol 2,4-cyclopyrophosphate synthase is required. It is obtained by expressing the gene ygbB of *E. coli* as described herein.

Steps (a) to (e) may be carried out as separate steps, optionally with intermediate isolation or as a one-pot reaction.

This synthesis may be carried out with any desired labelling, notably with deuterium, tritium; 13-carbon, 14-carbon or 32-phosphorus. Preferred for the purposes of the present invention is a total or partial labelling of 2C-methyl-D-erythritol 2,4-cycloprophosphate with 13-carbon for the purpose of analytical discrimination or a labelling with 14-carbon or 32-phosphorus for the purpose of detection, whereby the 13-carbon labelling and the radioactive labelling may be combined.

Total $^{13}$C-labelling can be carried out advantageously starting from [U-$^{13}$C$_6$] glucose and [U-$^{13}$C$_3$] sodium pyruvate or [2,3-$^{13}$C$_2$] pyruvate. In the presence of thiamine pyrophosphate, ATP and MgCl$_2$ the following enzymes are used for preparing [U-$^{13}$C$_5$]1-deoxy-D-xylulose 5-phosphate: triose phosphate isomerase, hexokinase, phosphoglucose isomerase, phosphofructokinase, aldolase and 1-deoxy-D-xylulose 5-phosphate synthase. Subsequently, the product can be converted to [U-$^{13}$C$_5$]2C-methyl-D-erythritol 4-phosphate with 1-deoxy-D-xylulose 5-phosphate reductoisomerase, glucose dehydrogenase and glucose, NADP$^+$ and MgCl$_2$.

Further [U-$^{13}$C$_5$]2C-methyl-D-erythritol 4-phosphate can be converted into [U-$^{13}$C$_5$]4-diphosphocydidyl-2C-methyl-D-erythritol, [U-$^{13}$C$_5$]4-diphosphocytidyl-2C-methyl-D-erythritol 2-phosphate and [U-$^{13}$C$_5$]2C-methyl-D-erythritol 2,4-cyclopyrophosphate using the enzymes YgbP, YchB and YgbB in the presence of CTP, ATP, MgCl$_2$ and MnCl$_2$. For regeneration of ATP it is possible to use also pyruvate kinase in the presence of phosphoenol pyruvate.

Downstream Intermediates

It has been surprisingly found that an intermediate of the non-mevalonate pathway, downstream from 2C-methyl-D-erythritol 2,4-cyclopyrophosphate can be produced by using the latter compound as starting material and cells or portions of cells as catalyst.

The cells used for producing the catalyst may be cells of any organism endowed with the non-mevalonate pathway, notably cells of plants, protists, like *Plasmodium falciparum* or bacteria. It is possible to use plastids instead of plant cells. A plant cell culture, for example of *Catharanthus roseus* may be used.

In one preferred embodiment plastids of plants are used. The plastids may be chromoplasts, chloroplasts, etioplasts or leucoplasts.

The plastids may be obtained from plant tissue by disruption of the cells, filtration and centrifugation according to known methods by e.g. Camara (Methods Enzymol. 214, 352–365 (1993)) or Liedvogel (Cytobiology 12, 155–174 (1976)). These publications also disclose incubation media for these plastids.

The incubation may be carried out in any incubation medium suitable for incubating plastid or cell suspensions. It is merely required that the metabolism is operative at least to the extent of the alternative biosynthetic pathway. The incubation medium should support the metabolism. In the simplest and most preferred case the incubation medium should not inhibit the reactions involved and all cofactors would be provided by the plastids or cells. It is also possible to add one or several cofactors to the incubation medium. The pH of the incubation medium should be physiologically suitable, preferably in the range of 5 to 9 and especially in the range of 7 to 8.

Since the plastids are biochemically fully competent they will provide any additional components for the biosynthesis. It is preferred but not mandatory to add a magnesium salt and/or a divalent manganese salt for bringing the enzymes to optimum activity and it is further preferred to add NADPH and/or NADP each in concentrations of 0.5 to 4 mM preferably 1 to 2 mM. Further FAD may be added in a concentration of preferably 1 to 100 μM, especially 5 to 50 μM. It is advantageous to add NaF in order to block phosphatases. The concentration of NaF is preferably 1 to 20 mM.

The plastids or cells isolated by methods known per se may be completely uninjured or more or less injured, even to the extent of being at least partially disrupted. The biochemical competence and the success of the screening procedure is largely independent of such differences and quite robust.

It has been surprisingly found that 2C-methyl-D-erythritol 2,4-cyclopyrophosphate is taken up by plastids.

In another preferred embodiment plant cells or preferably plastids thereof; or bacterial cells such as *E. coli*, notably strain M15 (pREP4), are grown and harvested by centrifugation; and subsequently resuspended for disruption. Any conventional disruption method may be used. A preferred disruption method makes use of an incubation with lysozyme in an appropriate medium. The medium may for example comprise tris hydrochloride, pH 7.5 to 8.5, preferably pH 8.0 as well as $MgCl_2$ (e.g. 5 to 20 mM) and dithiothreitol (e.g. 2 to 10 mM).

Subsequently, the reaction mixture is cooled and sonified. The obtained mixture is centrifuged to produce a pellet of solid components. It was surprisingly found that the enzymatic activity for the conversion of 2C-methyl-D-erythritol 2,4-cyclopyrophosphate is located in the solid cell fraction. Therefore, this solid cell fraction is resuspended in an appropriate medium (preferably the same as above).

It is possible to separate the solid cell fraction further in subfractions. This may be accomplished by conventional methods, for example, by differential centrifugation or centrifugation with density gradients.

Subsequently, 2C-methyl-D-erythritol 2,4-cyclopyrophosphate is added to this suspension. For detection purposes it is preferred to include radioactively labelled 2C-methyl-D-erythritol 2,4-cyclopyrophosphate. It may by T-, $^{14}C$- or $^{32}P$-labelled. For example, it may be labelled with $^{14}C$ in position 2.

It is also possible to use a totally $^{13}C$-labelled starting material for facilitating structural characterization of the product. To this end a small proportion of radioactive (e.g. $^{14}C$-labelled) starting material may be added.

The mixture is incubated, preferably at 30 to 45° C. and especially at 37° C. during a predetermined period of time, e.g. 2 to 20 h, especially 4 to 12 h, more preferably 5 to 8 h.

It is preferable to add a cobalt-II salt, notably $CoCl_2$. The concentration of the cobalt-II salt should be preferably 1 to 30 mM and more preferably 2 to 10 mM and especially about 5 mM. It has been surprisingly found that the cobalt-II salt leads to an increased concentration of produced intermediate. The mechanism is presently not clear. It may be contemplated that the cobalt ions serve as promotor for an enzyme for the synthesis of the intermediate or as an inhibitor for a subsequent enzyme.

After cultivation, the mixture is centrifuged (optionally after disruption of the cells or plastids) and the aqueous supernatant is analyzed. For this purpose, it may be concentrated e.g. by lyophilization. Aliquots of the concentrate may be analyzed by chromatography, notably high performance liquid chromatography (HPLC). It is preferred to employ ion pair, reversed phase HPLC. As a column, it is possible to use a Multospher 120 RP 18 column (5 μm crystalline silica gel, 4.6×250 mm, CS-Chromatographie Service GmbH, Langerwehe, Germany). For establishing ion pair conditions the column should be equilibrated with an aqueous solution of a tetra-alkylammonium salt, preferably tetra-n-butylammonium salt, whereby a conventional anion, e.g. chloride or hydrogen sulfate may be used. The column development may be effected with an aqueous solution (e.g. 5 to 20, preferably 10 mM) of the above tetra-alkylammonium salt, whereby a (preferably linear) gradient of a water-soluble solvent, e.g. methanol may be used, e.g. from 0 to 42% (v/v) of methanol. The effluent is monitored with an appropriate detector, notably a radiodetector in the case of radiolabelled starting material.

It has been observed that 2C-methyl-D-erythritol 2,4-cyclopyrophosphate is converted under the above conditions into a new intermediate which is distinct from the starting material and also from IPP and DMAPP. It has a retention volume between the retention volumes of 2C-methyl-D-erythritol 2,4-cyclopyrophosphate and IPP. Moreover, when the reaction is followed over time the lowering of the peak of 2C-methyl-D-erythritol 2,4-cyclopyrophosphate is clearly correlated with an increase of the product peak.

Enzymes of the Isoprenoid Pathway

We have previously demonstrated that the *E. coli* enzymes YgbP, YchB and YgbB and homologous enzymes in other organisms are in charge of the conversion of 2C-methyl-D-erythritol 4-phosphate to 2C-methyl-D-erythritol 2,4-cyclopyrophosphate via 4-diphosphocytidyl-2C-methyl-D-erythritol and diphosphocytidyl-2C-methyl-D-erythritol 2-phosphate.

We have now used a set theoretical approach to determine a set of enzymes in which with very high likelihood the enzymes operating downstream from 2C-methyl-D-erythritol 2,4-cyclopyrophosphate and upstream of IPP and/or DMAPP are situated. This has been accomplished by determining the genes which have the same taxonomic distribution as ygbP, ychB and ygbB. Specifically, a first subset of genes (intersection) is determined which are common to the sequenced genomes of all "positive" organisms which are known to be endowed with the non-mevalonate pathway. ygbP, ychB and ygbB were found to be members of said first subset. Next, "negative" organisms like *Saccharomyces cerevisiae* are selected which are known to lack the non-mevalonate pathway. Thereafter, a second subset of genes is determined by subtracting from the first subset those genes which have a homologous in the negative organisms. Thereafter a third subset was formed by substracting from the second subset any genes coding for proteins with well established known function. The remaining narrowest subset consists of the *E. coli* genes gcpE and lytB as designated in the *E. coli* genome. The taxonomic distribution of these two genes is shown in Tables 1 and 2.

A slightly broader set of four enzymes includes additionally the *E. coli* genes yjeE and ybeB. The taxonomic distribution of these two genes is shown in Tables 3 and 4.

TABLE 1

Occurrence of orthologous gcpE sequences in various organisms

| Organism | Corresponding to gcpE[a] Accession number, basepairs |
|---|---|
| *Aquifex aeolicus* VF5 | gb[b] AE000745, 352–1425 |
| *Bacillus subtilis* 168 | emb[c] Z99116, 193139–194272 |
| *Chlamydia pneumoniae* CWL029 | gb AE001621, 8026–9867 |
| *Chlamydia trachomatis* D/UW-3/CX | gb AE001280, 4785–6593 |
| *Deinococcus radiodurans* | gb AE001898, 7744–9033 |
| *Escherichia coli* K-12 MG1655 | gb AE000338, 372–1204 |
| *Haemophilus influenzae* Rd | gb U32712, 1613–2719 |
| *Helicobacter pylori* strain 26695 | gb AE000577, 90–1169 |
| *Helicobacter pylori* strain J99 | gb AE001490, 107–1186 |
| *Mycobacterium leprae* | gb L78824, 16209–17186 |
| *Mycobacterium tuberculosis* H37Rv | emb AL008883, 10845–12008 |

TABLE 1-continued

Occurrence of orthologous gcpE sequences in various organisms

| Organism | Corresponding to gcpE[a] Accession number, basepairs |
|---|---|
| Streptomyces coelicor A3(2) | emb AL049485, 15496–16650 |
| Synechocystis sp. PCC6803 | dbj[d] D90908, 73164–74375 |
| Thermotoga maritima | gb AE001754, 6801–8306 |
| Treponema pallidum | gb AE001221, 10202–11416 |

[a]http://www.ncbi.nlm.nih.gov
[b]GenBank database
[c]european database
[d]database of Japan

TABLE 2

Occurrence of orthologous lytB sequences in various organisms

| Organism | Corresponding to lytB[a] Accession number, basepairs |
|---|---|
| Acinetobacter sp. BD413 | gb[b] AF027189, 264–1214 |
| Aquifex aeolicus VF5 | gb AE000754, 71–940 |
| Arabidopsis thaliana chromosome II BAC | emb[c] AL035521, 66098–68216 |
| Bacillus subtilis 168 | dbj[d] D84432, 122126–123070 |
| Burkholderia pseudomallei | gb AF098521, 236–1177 |
| Campylobacter jejuni NCTC 11168 | emb X89371, 1655–2488 |
| Chlamydia pneumoniae CWL029 | gb AE001682, 5359–6291 |
| Chlamydia trachomatis D/UW-3/CX | gb AE001359, 2001–2924 |
| Deinococcus radiodurans | gb AE002049, 12853–13860 |
| Escherichia coli K-12 MG1655 | gb AE000113, 5618–6565 |
| Haemophilus influenzae Rd | gb U32781, 8285–9229 |
| Helicobacter pylori strain J99 | gb AE001527, 7015–7839 |
| Helicobacter pylori strain 26695 | gb AE000556, 91–915 |
| Listeria monocytogenes | gb U17284, 2082<>2555 |
| Mycobacterium leprae | emb AL049491, 6002–7009 |
| Mycobacterium tuberculosis H37Rv | emb AL021897, 63983–64990 |
| Nicotiana tabacum | gb AF159699, 1<>504 |
| Pseudomonas aeruginosa | gb L76605, 6331<>6729 |
| Pseudomonas fluorescens | gb M35366, 1857 > 2396 |
| Synechocystis sp. PCC6803 | dbj D64000, 46364–47584 |
| Thermotoga maritima | gb AE001796, 3613–4440 |
| Treponema pallidum | gb AE001230, 1785–2915 |

[a]http://www.ncbi.nlm.nih.gov
[b]GenBank database
[c]european database
[d]database of Japan

TABLE 3

Occurrence of orthologous yjeE sequences in various organisms

| Organism | Corresponding to yjeE[a] Accession number, basepairs |
|---|---|
| Anabaena species PCC7120 | gb[b] AF046871, 990–1478 |
| Aquifex aeolicus VF5 | gb AE000710, 2932–3333 |
| Bacillus subtilis 168 | Dbj[d] D88802, 27672–28148 |
| Borrelia burgdorferi | gb AE001129, 5010–5423 |
| Bradyrhizobium japonicum | gb AF042096, 7016–7489 |
| Campylobacter jejuni NCTC 11168 | emb[c] AL139076, 361–768 |
| Chlamydia pneumoniae CWL029 | gb AE001648, 7612–8037 |
| Chlamydia trachomatis D/UW-3/CX | gb AE001324, 7590–8063 |
| Deinococcus radiodurans | gb AE002066, 2143–2589 |
| Escherichia coli K-12 MG1655 | gb AE000489, 3299–3760 |
| Erysipelothrix rhusiopathiae | dbj AB019247, 4372–4692 |
| Haemophilus influenzae Rd | gb U32692, 68–544 |
| Helicobacter pylori strain J99 | gb AE001097, 9098–9499 |
| Helicobacter pylori strain 26695 | gb AE000584, 8919–9320 |
| Lactococcus lactis | emb Z70730, 4572–4916 |
| Mycobacterium leprae | gb U00020, 6462–6947 |
| Mycobacterium tuberculosis H37Rv | emb Z77165, 27337–27843 |
| Neisseria meningitidis strain Z2491 | gb AF058689, 10961–11371 |
| Neisseria meningitidis strain Z4400 | gb AF194079, 1685–2095 |
| Rickettsia prowazekii | emb AJ235270, 11821–12255 |
| Streptomyces coelicor | emb AL031317, 21836–22282 |
| Synechocystis sp. PCC6803 | dbj D90914, 142000–142473 |
| Thermotoga maritima | gb AE001806, 7502–7987 |
| Treponema pallidum | gb AE001257, 7721–8128 |

[a]http://www.ncbi.nlm.nih.gov
[b]GenBank database
[c]european database
[d]database of Japan

TABLE 4

Occurrence of orthologous ybeB sequences in various organisms

| Organism | Corresponding to ybeB[a] Accession no., basepairs |
|---|---|
| Aquifex aeolicus VF5 | gb[b] AE000732, 4157–4486 |
| Bacillus subtilis 168 | emb[c] Z99117, 42657–43013 |
| Borrelia burgdorferi | gb AE001177, 8901–9260 |
| Campylobacter jejuni NCTC 11168 | emb AL139078, 116712–117038 |
| Chlamydia muridarum | gb AE002282, 5712–6071 |
| Chlamydia pneumoniae CWL029 | gb AE001671, 6617–6976 |
| Chlamydia trachomatis D/UW-3/CX | gb AE001349, 5715–6074 |
| Deinococcus radiodurans | gb AE002087, 4944–5294 |
| Escherichia coli K-12 MG1655 | gb AE000168, 6454–6663 |
| Haemophilus influenzae Rd | gb U32688, 11870–12178 |
| Helicobacter pylori strain J99 | gb AE001554, 2536–2877 |
| Helicobacter pylori strain 26695 | gb AE000642, 600–941 |
| Mycobacterium tuberculosis H37Rv | emb Z81368, 40124–40504 |
| Neisseria meningitidis strain MC58 | gb AE002552, 3227–3613 |
| Neisseria meningitidis strain Z2491 | emb AL162753, 46997–47383 |
| Rickettsia prowazekii | emb AJ235273, 148106–148432 |
| Streptomyces coelicor | emb AL136518, 16927–17373 |
| Synechocystis sp. PCC6803 | dbj[d] D90908, 56510–56974 |
| Thermotoga maritima | gb AE001700, 2645–2977 |
| Treponema pallidum | gb AE001245, 10516–10851 |

[a]http://www.ncbi.nlm.nih.gov
[b]GenBank database
[c]european database
[d]database of Japan With the functional assignments of YgbP, YchB and YgbB with the production of proteins having enzymatically competent folding structures, we have provided avenues for the production of the products of the enzymatic reaction of YgbP, YchB and YgbB, namely 4-diphosphocytidyl-2C-methyl-D-erythritol, 4-diphosphocytidyl-2C-methyl-D-erythritol 2-phosphate and 2C-methyl-D-erythritol 2,4-cyclopyrophosphate or salts thereof. Based on this achievement, we have opened new avenues for the inhibition of the alternative isoprenoid pathway in plants as well as bacteria and also in protozoa, like Plasmodium.

The designations of YgbP, YgbB and YchB in the *E. coli* genome are used herein also for the homologous proteins in other organisms.

We have found that in plants, notably *Arabidopsis thaliana* the enzymes homologous to YgbP, YchB and YgbB have a leader peptide not present in the bacterial enzymes. This leader peptide serves the purpose of transport of the enzyme into the plastids. Such specific leader sequence may be replaced by any other leader sequence from *A. thaliana* or from any other plant or it may also be eliminated.

The *A. thaliana* sequence of YgbP has been obtained by genome sequencing. We have sequenced the gene ygbP of *A.* thaliana and cloned the full-length gene from RNA. The cDNA sequence of the cloned ygbP gene from *A. thaliana* was different from the DNA sequence found in the database (gb AC004136) due to introns. The amino acid sequence corresponding to this cDNA is also different from the amino acid sequence given in the database (gb AC004136). This seems to be due to erroneous computational intron splicing from chromosomal DNA. The cDNA leader sequence was found to be identical to the database prediction.

The genes ygbP, ygbB and ychB of *E. coli* were obtained by PCR using primers with specific restriction sites. In this PCR reaction two recognition sites for restriction enzymes are introduced at the 5'-end and at the 3' end. The preferred recognition site is NcoI or EcoRI at the 5'-end and PstI at the 3' end. The amplified PCR fragment and an expression vector are digested with the same restriction enzymes and ligated together with T4-ligase to yield recombinant plasmid capable of autonomous replication in the host microorganism. The recombinant plasmid is used to transform the host microorganism. The preferred host is *E. coli*. The same method was used for the genes ygbP, ygbB and ychB of *Arabidopsis thaliana* and for ychB of tomato whereby the nucleotide sequence was modified for the codon usage of *E. coli* for highly expressed genes (without leader sequence).

Nucleic Acids, Vectors, Expression Systems and Polypeptides

In practicing the present invention, many techniques in molecular biology, microbiology, recombinant DNA, and protein biochemistry such as these explained fully in, for example, Sambrook et al., 1989, *Molecular Cloning, A Laboratory Manual*, Second Edition, Cold Spring Harbor Laboratory Press, Cold Spring Harbor, N.Y.; *DNA Cloning: A practical Approach*, Volumes I and II, 1985 (Glover, ed.); Oligonucleotide Synthesis, 1984, (Gait, ed.); Transcription and Translation, 1984 (Hames and Higgins, eds.); *A Practical Guide to Molecular Cloning*; the series *Methods in Enzymology* (Academic Press, Inc.); and *Protein Purtifcation: Principles and Practice*, Second Edition (Springer-Verlag, N.Y.) are used.

The present invention encompasses nucleic acid sequences encoding plant enzymes, enzymatically active fragments derived therefrom, and related derived sequences from other plant species. As used herein, a nucleic acid that is "derived from" a sequence refers to a nucleic acid sequence that corresponds to a region of the sequence, sequences that are homologous or complementary to the sequence, and "sequence-conservative variants" and "function-conservative variants".

Sequence-conservative variants are those in which a change of one or more nucleotides in a given codon position results in no alteration in the amino acid encoded at that position. Function-conservative variants are those in which a given amino acid residue has been changed without altering the overall conformation and function of the polypeptide, including, but not limited to, replacement of an amino acid with one having similar physico-chemical properties (such as, for example, acidic, basic, hydrophobic, and the like). Enzyme fragments that retain enzymatic activity can be identified according to the methods described herein, e.g, expression in *E. coli* followed by enzymatic assay of the cell extract.

Sequences derived from plants other than *Arabidopsis thaliana* can be isolated by routine experimentation using the methods and compositions provided herein. For example, hybridization of a nucleic acid comprising all or part of *Arabidopsis* sequence under conditions of intermediate stringency (such as, for example, an aqueous solution of 2×SSC at 65° C.) to cDNA or genomic DNA derived from other plant species can be used to identify homologues. cDNA libraries derived from different plant species are commercially available (Clontech, Palo Alto, Calif.; Stratagene, La Jolla, Calif.). Alternatively, PCR-based methods can be used to amplify related sequences from cDNA or genomic DNA derived from other plants. Expression of the identified sequence in, e.g. *E. coli*, using methods described in more detail herein, is then performed to confirm the enzymatic activity of the polypeptide encoded by the sequence. Accordingly, sequences derived from dicotyledonous and monocotyledenous plants are within the scope of the invention.

The nucleic acids of the present invention include purine- and pyrimidine-containing polymers of any length, either polyribonucleotides or polydeoxyribonucleotides or mixed polyribo-polydeoxyribo-nucleotides. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases. The nucleic acids may be isolated directly from cells. Alternatively, PCR can be used to produce the nucleic acids of the invention, using either chemically synthesized strands or genomic material as templates. Primers used for PCR can be sythesized using the sequence information provided herein and can further be designed to introduce appropriate new restriction sites, if desirable, to facilitate incorporation into a given vector for recombinant expression.

The nucleic acids of the present invention may be flanked by natural *Arabidopsis* regulatory sequences, or may be associated with heterologous sequences, including promoters, enhancers, response elements, signal sequences, polyadenylation sequences, introns, 5'- and 3'-noncoding regions and the like. The nucleic acids may also be modified by many means known in the art. Non-limiting examples of such modifications include methylation, "caps", substitution of one or more of the naturally occuring nucleotides with an analog, and internucleotide modifications such as, for example, those with uncharged linkages (e.g., methyl phosphonates, phosphotriesters, phosphoromidates, carbamates, etc.) and with charged linkages (e.g., phosphorothioates, phosphorodithioates, etc.). Nucleic acids may contain one or more additional covalently linked moieties, such as, for example, proteins (e.g., nucleases, toxins, antibodies, signal peptides, poly-L-Lysine, etc.), intercalators (e.g., acridine, psoralen, etc.), chelators (e.g., metals, radioactive metals, iron, oxidative metals, etc.), and alkylators. The nucleic acid may be derivatized by formation of a methyl or ethyl phosphotriester or an alkyl phosphoramidate linkage. Furthermore, the nucleic acid sequences of the present invention may also be modified with a label capable of providing a detectable signal, either directly or indirectly. Exemplary labels include radioisotopes, fluorescent molecules, biotin, and the like.

The invention also provides nucleic acid vectors comprising the disclosed sequences or derivatives or fragments thereof. A large number of vectors, including plasmid and fungal vectors, have been described for replication and/or expression in a variety of eukaryotic and prokaryotic hosts. Non-limiting examples include pKK plasmids (Clontech), pUC plasmids, pET plasmids (Novagen, Inc., Madison, Wis.), or pRSET or pREP (Invitrogen, San Diego, Calif.), and many appropriate host cells, using methods disclosed or cited herein or otherwise known to those skilled in the relevant art. Recombinant cloning vectors will often include one or more replication sytems for cloning or expression, one or more markers for selection in the host, e.g. antibiotic resistance, and one or more expression cassettes. Suitable host cells may be transformed/transfected/infected as appropriate by any suitable method including electroporation, $CaCl_2$ mediated DNA uptake, tungae infection, microinjection, miroprojectile, or other established methods.

Appropriate host cells include bacteria, archaebacteria, fungi, especially yeast, plant and animal cells, especially mammalian cells. Of particular interest are *E. coli, B. subtilis, Saccharomyces cerevisiae, Saccharomyces carlsbergensis, Schizosacchromyces pombi,* SF9 cells, C129 cells, 293 cells, *Neurospora,* and CHO cells, COS cells, HeLa cells, and immortalized mammalian myeloid and lyphoid cell lines. Preferred replication systems include M13, ColE1, SV40, baculovirus, lambda, adenovirus, and the like. A large number of transcription initation and termination regulatory regions have been isolated and shown to be effective in the transcription and translation of heterologous proteins in the various hosts. Examples of these regions, methods of isolation, manner of manipulation, etc. are known in the art. Under appropriate expression conditions, host cells can be used as a source of recombinantly produced enzyme-derived peptides and polypeptides.

Advantageously, vectors may also include a transcription regulatory element (i.e. a promoter) operably linked to the enzyme portion. The promoter may optionally contain operator portions and/or ribosome binding sites. Non-limiting examples of bacterial promoters compatible with *E. coli* include: trc promoter, β-lactamase (penicillinase) promoter; lactose promoter; tryptophan (trp) promoter; arabinose BAD operon promoter, lambda-derived $P_L$ promoter and N gene ribosome binding site; and the hybrid tac promoter derived from sequences of the trp and lac UV5 promoters. Non-limiting examples of yeast promoters include 3-phosphoglycerate kinase promoter, glyceraldehyde-3-phosphate dehydrogenase (GAPDH) promoter, galactokinase (GALI) promoter, galactoepimerase promoter, and alcohol dehydrogenase (ADH) promoter. Suitable promoters for mammalian cells include without limitation viral promoters such as that from Simian Virus 40 (SV40), Rous sarcoma virus (RSV), adenovirus (ADV), and bovine papilloma virus (BPV). Mammalian cells may also require terminator sequences and poly A addition sequences, and enhancer sequences which increase expression may also be included. Sequences which cause amplification of the gene may also be desirable. Furthermore, sequences that facilitate secretion of the recombinant product from cells, including, but not limited to, bacteria, yeast, and animal cells, such as secretory signal sequences and/or prohormone pro region sequences, may also be included.

Nucleic acids encoding wild-type or variant enzyme polypeptides may also be introduced into cells by recombination events. For example, such a sequence can be introduced into a cell, and thereby effect homologous recombination at the site of endogenous gene or a sequence with substantial identity to the gene. Other recombination-based methods, such as non-homologous recombinations or deletion of endogenous genes by homologous recombination, may also be used.

Enzyme-derived polypeptides according to the present invention, including function-conservative enzyme variants may be isolated from wild-type or mutant *Arabidopsis* cells, or from heterologous organisms or cells (including, but not limited to, bacteria, fungi, insect, plant, and mammalia cells) into which an enzyme-derived protein-coding sequence has been introduced and expressed. Furthermore, the polypeptides may be part of recombinant fusion proteins. Alternatively, polypeptides may be chemically synthesized by commercially available automated procedures, including, without limitation, exclusive solid phase synthesis, partial solid phase methods, fragment condensation or classical solution synthesis.

"Purification" of an enzyme polypeptide refers to the isolation of the enzyme polypeptide in a form that allows its enzymatic activity to be measured without interference by other components of the cell in which the polypeptide is expressed. Methods for polypeptide purification are well-known in the art, including, without limitation, preparative disc-gel electrophoresis, isoelectric focusing, reversed-phase HPLC, gel filtration, ion exchange and partition chromatography, and countercurrent distribution. For some purposes, it is preferable to produce the polypeptide in a recombinant system in which the protein contains an additional sequence tag that facilitates purification, such as, but not limited to, a polyhistidine sequence. The polypeptide can then be purified from a crude lysate of the host cell by chromatography on an appropriate solid-phase matrix. Alternatively, antibodbies produced against the enzyme or against peptides derived therefrom can be used as purification reagents. Other purification methods are possible.

The present invention also encompasses derivatives and homologues of the enzyme polypeptides. For some purposes, nucleic acid sequences encoding the peptides may be altered by substitutions, additions, or deletions that provide for functionally equivalent molecules, i.e., function-conservative variants. For example, one or more amino acid residues within the sequence can be substituted by another amino acid of similar properties, such as, for example, positively charged amino acids (arginine, lysine, and histidine); negatively charged amino acids (aspartate and glutamate); polar neutral amino acids; and non-polar amino acids.

The designations of YgbP, YgbB and YchB in the *E. coli* genome are used herein also for the homologous proteins in other organisms.

The isolated polypeptides may be modified by, for example, phosphorylation, sulfation, acylation, or other protein modifications. They may also be modified with a label capable of providing a detectable signal, either directly or indirectly, including, but not limited to, radioisotopes and fluorescent compounds.

Genes corresponding to YgbP (or YgbB) or YchB from any plant may be readily isolated by well known techniques, for example by Southern hybridization or by PCR using degenerated primers. Notably, a cDNA library of this plant in question is screened using the nucleic acid direct labelling and detection system kit supplied from Amersham-Pharmacia-Biotech (Heidelberg, Germany). Hybridization conditions are for example 7% sodium dodecyl sulfate (SDS). Positively hybridizing plaques are detected by luminescence detection (or in other systems by autoradiography). After purification to single plaques, cDNA inserts are isolated, and their sequences determined by the chain termination method using dideoxy terminators labeled with fluorescent dyes (Applied Biosystems, Inc., Foster City, Calif.). This experimental protocol can be used by one of ordinary skill in the art to obtain genes substantially similar to the *Arabidopsis* gene from any other plant species.

Screening Methods to Identify Enzyme Inhibitors/Herbicides

The methods and compositions of the present invention can be used to identify compounds that inhibit the function of the enzymes and thus are for example useful as herbicides or as lead compounds for the development of useful herbicides. This may be achieved by providing a cell that expresses the enzyme and thereby produces cell cultures expressing the enzyme which are incubated in the presence of test compounds to form test cultures, and in the absence of test compounds to form control cultures. Incubation is allowed to proceed for a sufficient time and under appropriate conditions to allow for interference with enzyme function. At a predetermined time after the start of incubation with a test compound, an assay is performed to monitor enzymatic activity. In one embodiment, enzyme activity is monitored in whole cells. Alternatively, enzymatic activity may be monitored in cell extracts or media containing the isolated enzyme using assays such as that described below. Additional controls, with respect to both culture samples and assay samples, are also included, such as, for example, a host cell not expressing the enzyme (e.g., a host cell transformed with an expression plasmid containing the enzyme gene in a reverse orientation or with no insert). Enzyme inhibitory compounds are identified as those that reduce enzyme activity in the test cultures relative to the control cultures.

Host cells that may be used in practicing the present invention include without limitation bacterial, fungal, insect, mammalian, and plant cells. Preferably, bacterial cells are used. Most preferably, the bacterial cell is a variant (such as, e.g. the imp mutant of *E. coli*) that exhibits increased membrane permeability for test compounds relative to a wild-type host cell.

Preferably, the methods of the present invention are adapted to a high-throughput screening, allowing a multiplicity of compounds to be tested in a single assay. Such inhibitory compounds may be found in, for example, natural product libraries, fermentation libraries (encompassing plants and microorganisms), combinatorial libraries, compound files, and synthetic compound libraries. For example, synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich Chemical Company, Inc. (Milwaukee, Wis.). Alternatively, libraries of natural compounds in the form of bacterial, fungal, plant, and animal extracts are available from, for example, Pan Laboratories (Bothell, Wash.) or MycoSearch (NC), or are readily producible. Additionally, natural and synthetically produced libraries and compounds are readily modified through conventional chemical, physical, and biochemical means (Blondell et al. TibTech 14, 60 (1996)). Inhibitor assays according to the present invention are advantageous in accommodating many different types of solvents and thus allowing the testing of compounds from many sources.

Once a compound has been identified by the methods of the present invention as inhibitor, in vivo and in vitro tests may be performed to further characterize the nature and mechanism of the inhibitory activity. The effect of an identified compound on in vitro enzymatic activity of purified or partially purified protein may be determined and enzyme kinetic plots may be used to distinguish, e.g., competitive and non-competitive inhibitors.

Compounds identified as inhibitors using the methods of the present invention may be modified to enhance potency, efficacy, uptake, stability, and suitability for use in commercial herbicide applications, etc. These modifications are achieved and tested using methods well-known in the art.

Isolation of Herbicide-Resistant Enzyme Variants

The present invention encompasses the isolation of enzyme variants that are resistant to the action of enzyme inhibitors/herbicides. The enzyme variants may be naturally occurring or may be obtained by random or site-directed mutagenesis.

In one embodiment, a population of cells or organisms expressing the enzyme of interest is mutagenized using procedures well-known in the art, after which the cells or organisms are subjected to a screening or selection procedure to identify those that are resistant to the toxic effects of an inhibitor. The variant enzyme gene is then isolated from the resistant cell or organism using, e.g., PCR techniques.

In another embodiment, an isolated enzyme gene is subjected to random or site-directed mutagenesis in vitro, after which mutagenized versions of the gene are reintroduced into an appropriate cell such as, e.g., *E. coli*, and the cells are subjected to a selection or screening procedure as above.

The variant enzyme genes are expressed in an appropriate host cell, and the enzymatic properties of variant enzyme polypeptides are compared to the wild-type enzyme. Preferably, a given mutation results in an enzyme variant polypeptide that retains in vitro enzymatic activity, while exhibiting catalytic activity that is relatively more resistant to the selected herbicide(s) than is wild-type enzyme. Preferably, when expressed in a cell that requires enzyme activity for viability, the variant exhibits (i) catalytic activity alone sufficient to maintain the viability of a cell in which it is expressed; or catalytic activity in combination with any herbicide resistant enzyme variant protein also expressed in the cell, which may be the same as or different than the first enzyme protein, sufficient to maintain the viability of a cell in which it is expressed; and (ii) catalytic activity that is more resistant to the herbicide than is wild-type enzyme.

Therefore, any one specific enzyme variant protein need not have the total catalytic activity necessary to maintain the viability of the cell, but must have some catalytic activity in an amount, alone or in combination with the catalytic activity of additional copies of the same enzyme variant and/or the catalytic activity of other enzyme variant protein(s), sufficient to maintain the viability of a cell that requires enzyme activity for viability. For example, catalytic activity may be increased to minimum acceptable levels by introducing multiple copies of a variant encoding gene into the cell or by introducing the gene which further includes a relatively strong promoter to enhance the production of the variant.

More resistant means that the catalytic activity of the variant is diminished by the herbicide(s), if at all, to a lesser degree than wild-type enzyme catalytic activity is diminished by the herbicide(s). Preferred more resistant variant enzyme retains sufficient catalytic activity to maintain the viability of a cell, plant, or organism wherein at the same concentration of the same herbicide(s), wild-type enzyme would not retain sufficient catalytic activity to maintain the viability of the cell, plant or organism.

Preferably, the catalytic activity in the absence of herbicide(s) is at least about 5% and, most preferably, is more than about 20% of the catalytic activity of the wild-type enzyme in the absence of herbicide(s).

Herbicide-resistant enzyme variants can be used as genetic markers in any cell that is normally sensitive to the inhibitory effects of the herbicide formation. In one embodiment, DNA encoding an herbicide-resistant enzyme variant is incorporated into a plasmid under the control of a suitable promoter. Any desired gene can then be incorporated into the plasmid, and the final recombinant plasmid introduced into an herbicide-sensitive cell. Cells that have been transformed with the plasmid are then selected or screened by incubation in the presence of a concentration of herbicide sufficient to inhibit growth and/or pigment formation.

Chemical-Resistant Plants and Plants Containing Variant Enzyme Genes

The present invention encompasses transgenic cells, including, but not limited to seeds, organisms, and plants into which genes encoding herbicide-resistant enzyme variants have been introduced. Non-limiting examples of suitable recipient plants are listed in Table 5 below:

TABLE 5

RECIPIENT PLANTS

| COMMON NAME | FAMILY | LATIN NAME |
| --- | --- | --- |
| Maize | Gramineae | Zea mays |
| Maize; Dent | Gramineae | Zea mays dentiformis |
| Maize; Flint | Gramineae | Zea mays vulgaris |
| Maize, Pop | Gramineae | Zea mays microsperma |
| Maize, Soft | Gramineae | Zea mays amylacea |
| Maize, Sweet | Gramineae | Zea mays amyleasaccharata |
| Maize, Sweet | Gramineae | Zea mays saccharate |
| Maize, Waxy | Gramineae | Zea mays ceratina |
| Wheat, Dinkel | Pooideae | Triticum spelta |
| Wheat, Durum | Pooideae | Triticum durum |
| Wheat, English | Pooideae | Triticum turgidum |
| Wheat, Large Spelt | Pooideae | Triticum spelta |
| Wheat, Polish | Pooideae | Triticum polonium |
| Wheat, Poulard | Pooideae | Triticum turgidum |
| Wheat, singlegrained | Pooideae | Triticum monococcum |
| Wheat, Small Spelt | Pooideae | Triticum monococcum |
| Wheat, Soft | Pooideae | Triticum aestivum |
| Rice | Gramineae | Oryza sativa |
| Rice, American Wild | Gramineae | Zizania aquatica |
| Rice, Australian | Gramineae | Oryza australiensis |
| Rice, Indian | Gramineae | Zizania aquatica |
| Rice, Red | Gramineae | Oryza glaberrima |
| Rice, Tuscarora | Gramineae | Zizana aquatica |
| Rice, West African | Gramineae | Oryza glaberrima |
| Barley | Pooideae | Hordeum vulgare |
| Barley, Abyssinian intermediate, also Irregular | Pooideae | Hordeum irregulare |
| Barley, Ancestral Tworow | Pooideae | Hordeum spontaneum |
| Barley, Beardless | Pooideae | Hordeum trifurcatum |
| Barley, Egyptian | Pooideae | Hordeum trifurcatum |
| Barley, fourrowed | Pooideae | Hordeum vulgare polystichon |
| Barley, sixrowed | Pooideae | Hordeum vulgare hexastichon |
| Barley, Tworrowed | Pooideae | Hordeum distichon |
| Cotton, Abroma | Dicotyledoneae | Abroma augusta |
| Cotton, American Upland | Malvaceae | Gossypium hirsutum |
| Cotton, Asiatic Tree also Indian Tree | Malvaceae | Gossypium arboreum |
| Cotton, Brazilian, also, Kidney, and, Pernambuco | Malvaceae | Gossypium barbadense brasiliense |
| Cotton, Levant | Malvaceae | Gossypium herbaceum |
| Cotton Long Silk, also Long Staple, Sea Island | Malvaceae | Gossypium barbadense |
| Cotton Mexican, also Short Staple | Malvaveae | Gossypium hirsutum |
| Soybean, Soya | Leguminosae | Glycine max |
| Sugar beet | Chenopodiaceae | Beta vulgaris altissima |
| Sugar cane | Woody-plant | Arenga pinnata |
| Tomato | Solanaceae | Lycopersicon esculentum |

TABLE 5-continued

RECIPIENT PLANTS

| COMMON NAME | FAMILY | LATIN NAME |
| --- | --- | --- |
| Tomato, Cherry | Solanaceae | Lycopersicon esculentum cerasiforme |
| Tomato, Common | Solanaceae | Lycopersicon esculentum commune |
| Tomato, Currant | Solanaceae | Lycopersicon pimpinellifolium |
| Tomato, Husk | Solanaceae | Physalis ixocarpa |
| Tomato, Hyenas | Solanaceae | Solanum incanum |
| Tomato, Pear | Solanaceae | Lycopersicon esculentum pyriforme |
| Tomato, Tree | Solanaceae | Cyphomandra betacea |
| Potato | Solanaceae | Solanum tuberosum |
| Potato, Spanish, Sweet potato | Convolvulaceae | Ipormoca batatas |
| Rye, Common | Pooideae | Secale cereale |
| Rye, Mountain | Pooideae | Secale montanum |
| Pepper, Bell | Solanaceae | Capsicum annuum grossum |
| Pepper, Bird, also Cayenne, Guinea | Solanaceae | Capsicum annuum minimum |
| Pepper, Bonnet | Solanaceae | Capsicum sinense |
| Pepper, Bullnose, also Sweet | Solanaceae | Capsicum annuum grossum |
| Pepper, Cherry | Solanaceae | Capiscum annuum cerasiforme |
| Pepper, Cluster, also Red Cluster | Solanaceae | Capsicum annuum fasciculatum |
| Pepper, Cone | Solanaceae | Capsicum annuum conoides |
| Pepper, Goat, also Spur | Solanaceae | Capsicum frutescens |
| Pepper, Long | Solanaceae | Capsicum frutescens longum |
| Pepper, Ornamental Red, also Wrinkled | Solanaceae | Capsicum annuum abbreviatum |
| Pepper, Tabasco Red | Solanaceae | Capsicum annuum conoides |
| Lettuce, Garden | Compositae | Lactuca sativa |
| Lettuce, Asparagus, also Celery | Compositae | Lactuca sativa asparagina |
| Lettuce, Blue | Compositae | Lactuca perennis |
| Lettuce, Blue, also Chicory | Compositae | Lactuca pulchella |
| Lettuce, Cabbage, also Head | Compositae | Lactuca satica capitata |
| Lettuce, Cos, also Longleaf, Romain | Compositae | Lactuca sativa longifolia |
| Lettuce, Crinkle, also Curled, Cutting, Leaf | Compositae | Lactuca sativa crispa |
| Celery | Umbelliferae | Apium graveolens dulce |
| Celery, Blanching, also Garden | Umbelliferae | Apium graveolens dulce |
| Celery, Root, also Turniproote | Umbelliferae | Apium graveolens rapaceum |
| Eggplant, Garden | Solanaceae | Solanum melongena |
| Sorghum | Sorghum | All crop specie |
| Alfalfa | Leguminosae | Medicago sativum |
| Carrot | Umbelliferae | Daucus carota sativa |
| Bean, Climbing | Leguminosae | Phaseolus vulgaris vulgaris |
| Bean, Sprouts | Leguminosae | Phaseolus aureus |
| Bean, Brazilian Broad | Leguminosae | Canavalia ensiformis |
| Bean, Broad | Leguminosae | Vicia faba |
| Bean, Common, also French, White, Kidney | Leguminosae | Phaseolus vulgaris |
| Bean, Egyptian | Leguminosae | Dolichos lablab |
| Bean, Long, also Yardlong | Leguminosae | Vigna sesquipedalis |
| Bean, Winged | Leguminosae | Psophocarpus teragonolobus |
| Oat, also Common, Side, Tree | Avena | Sativa |
| Oat, Black, also Bristle, Lopsided | Avena | Strigosa |
| Oat, Bristle | Avena | |

TABLE 5-continued

RECIPIENT PLANTS

| COMMON NAME | FAMILY | LATIN NAME |
|---|---|---|
| Pea, also Garden, Green, Shelling | Leguminosae | Pisum, sativum sativum |
| Pea, Blackeyed | Leguminosae | Vigna sinensis |
| Pea, Edible Podded | Leguminosae | Pisum sativum axipluum |
| Pea, Grey | Leguminosae | Pisum sativum speciosum |
| Pea, Winged | Leguminosae | Tetragonolobus purpureus |
| Pea, Wrinkled | Leguminosae | Pisum sativum meduilare |
| Sunflower | Compositae | Helianthus annuus |
| Squash, Autumn, Winter | Dicotyledoneae | Cucurbita maxima |
| Squash, Bush, also Summer | Dicotyledoneae | Cucurbita pepo melopepo |
| Squash, Turban | Dicotyledoneae | Cucurbita maxima turbaniformis |
| Cucumber | Dicotyledoneae | Cucumis sativus |
| Cucumber, African, also Bitter | | Momordica charantia |
| Cucumber, Squirting, also Wild | | Ecbalium elaterium |
| Cucumber, Wild | | Cucumis anguria |
| Poplar, California | Woody-Plant | Populus trichocarpa |
| Poplar, European Black | | Populus nigra |
| Poplar, Gray | | Populus canescens |
| Poplar, Lombardy | | Populus italica |
| Poplar, Silverleaf, also White | | Populus alba |
| Poplar, Wester Balsam | | Populus trichocarpa |
| Tobacco | Solanaceae | Nicotiana |
| Arabidopsis Thaliana | Cruciferae | Arabidopsis thaliana |
| Turfgrass | Lolium | |
| Turfgrass | Agrostis | |
| | Other families of turfgrass | |
| Clover | Leguminosae | |

Expression of the variant polypeptides in transgenic plants confers a high level of resistance to herbicides allowing the use of these herbicides during cultivation of the transgenic plants.

Methods for the introduction of foreign genes into plants are known in the art. Non-limiting examples of such methods include *Agrobacterium infection*, particle bombardment, polyethylene glycol (PEG) treatment of protoplasts, electroporation of protoplasts, microinjection, macroinjection, tiller injection, pollen tube pathway, dry seed inhibition, laser perforation, and electrophoresis. These methods are described in, for example, Jenes et al., and Ritchie et al. In: Transgenic Plants, Vol. 1, Engineering and Utilization, (Kung and Wu, eds.), Academic Press, Inc., Harcourt Brace Jovanovich 1993; and Mannonen et al., Critical Reviews in Biotechnology, 14, 287–310 (1994).

In a preferred embodiment, the DNA encoding a variant enzyme is cloned into a DNA vector containing an antibiotic resistance marker gene, and the recombinant enzyme DNA-containing plasmid is introduced into *Agrobacterium tumefaciens* containing a Ti plasmid. This "binary vector system" is described in, for example, U.S. Pat. No. 4,490,838 and in An et al. (Plant Mol. Biol. Manual A3 1–19 (1988)). The transformed *Agrobacterium* is then co-cultivated with leaf disks from the recipient plant to allow infection and transformation of plant cells. Transformed plant cells are then cultivated in regeneration medium, which promotes the formation of shoots, first in the presence of the appropriate antibiotic to select for transformed cells, then in the presence of herbicide. In plant cells successfully transformed with DNA encoding herbicide-resistant enzyme, shoot formation occurs even in the presence of levels of herbicide that inhibit shoot formation from non-transformed cells. After confirming the presence of variant enzyme DNA using, for example, polymerase chain reaction (PCR) analysis, transformed plants are tested for their ability to withstand herbicide spraying and for their capabilities for seed germination and root initiation and proliferation in the presence of herbicide.

The methods and compositions of the present invention can be used for the production of herbicide-resistant enzyme variants, which can be incorporated into plants to confer selective herbicide resistance on the plants. Intermediate variants of enzyme (for example, variants that exhibit sub-optimal specific activity but high herbicide resistance, or the converse) are useful as templates for the design of second-generation enzyme variants that retain adequate specific activity and high resistance.

Herbicide resistant enzyme genes can be transformed into crop species in single or multiple copies to confer herbicide resistance. Genetic engineering of crop species with reduced sensitivity to herbicides can:

(1) Increase the spectrum and flexibility of application of specific effective and environmentally benign herbicides;
(2) Enhance the commercial value of these herbicides;
(3) Reduce weed pressure in crop fields by effective use of herbicides on herbicide resistant crop species and a corresponding increase in harvest yields;
(4) Increase sales of seed for herbicide resistant plants;
(5) Increase resistance to crop damage from carry-over of herbicides applied in previous planting;
(6) Decrease susceptibility to changes in herbicide characteristics due to adverse climate conditions; and
(7) Increase tolerance to unevenly or mis-applied herbicides.

For example, plants containing transgenic enzyme variant protein can be cultivated. The crop can be treated with a weed controlling effective amount of the herbicide to which the enzyme variant transgenic plant is resistant, resulting in weed control in the crop without detrimentally affecting the cultivated crop.

The compounds detected as inhibitors by the above screening methods may be used as pure compounds or in combination together with appropriate additives for inhibiting the enzymes in plant, bacterial or protozoal organisms. Conventional additives in the field of herbicides, antibacterial agents or antiprotozoal agents may be used.

The invention shall now be described with reference to specific examples.

REFERENCE EXAMPLE 1

2.0 µg of the vector pQE30 (Qiagen, Hilden, Germany) is digested with 30 U of NcoI (New England Biolabs (NEB), Schwalbach, Germany) in a total volume of 60 µl containing 6 µl of NEB4 buffer. The reaction mix is incubated for 3 h at 37° C. After adding 33 µM of each dNTP (NEB) and 5 U Kienow fragment of polymerase I from *E. coli* (NEB) the reaction mix is incubated for additional 30 min at 25° C. The vector DNA is purified using the PCR purification kit from Qiagen. 500 µl of buffer PB (Qiagen) is added to 98 µl of PCR reaction mixture and applied to a Qiaquick column and centrifuged for 1 min at 14,000 rpm. The flow through is discarded. 0.75 ml of buffer PE (Qiagen) is loaded on the column and centrifuged as before. The flow through is discarded and the column is centrifuged for an additional 1 min at 14,000 rpm. The column is placed in a clean 1.5 ml eppendorf tube. 50 µl of H$_2$O (redistilled, sterile) is added to the column and it is centrifuged for 1 min at 14,000 rpm. The flow through contained 1.5 µg of purified vector DNA.

20 ng of vector DNA is religated with 1 U of T4-Ligase from Gibco-BRL (Eggenstein, Germany), 2 µl of T4-Ligase buffer (Gibco-BRL) in a total volume of 10 µl yielding the plasmid pQE_noNco. The ligation mixture is incubated overnight at 4° C. With 2 µl of the ligation mixture electrocompetent *E. coli* XL1-Blue (Bullock et al. XL1-Blue: a high efficiency plasmid transforming recA *Escherichia coli* with β-galactosidase selection. BioTechniques 5, 376–379 (1987); commercial source: Stratagene, LaJolla, Calif., U.S.A.) cells are transformed.

Preparation of Electrocompetent Cells: 1 liter of Luria Bertani (LB) medium is inoculated 1:100 with fresh overnight culture. The cells are grown at 37° C. with shaking at 220 rpm to an optical density of 0.5 at 600 nm. The cells are chilled on ice for 20 min and centrifuged for 15 min at 4,000 rpm at 4° C. The supernatant is removed and the pellet is resuspended in 1 liter of ice-cold sterile 10% (v/v) glycerol. The cells are centrifuged two times as described before resuspending the cells in 0.5 liter and in 20 ml of ice-cold sterile 10% (v/v) glycerol, respectively. The cells are centrifuged an additional time and the pellet is resuspended in a volume of 2 ml of ice-cold 10% (v/v) glycerol. This suspension is frozen in aliquots of 80 µl and stored in liquid nitrogen.

Electro-Transformation Using the Gene Pulser Apparatus from Biorad (Munich, Germany): The electrocompetent cells are thawed on ice. 40 µl of the cell suspension are mixed with 2 µl of ligation mixture and transferred into a prechilled, sterile 0.2 cm cuvette (Biorad). The suspension is shaked to the bottom and the cuvette is placed into the prechilled chamber slide. The chamber slide is pushed into the chamber and the cells are pulsed at 2.50 kV, 25 µF and Pulse Controller setting 200 Ω. The cuvette is removed from the chamber and the cells are suspended in 1 ml of SOC medium (2% (w/v) casein hydrolysate, 0.5% (w/v) yeast extract, 10 mM NaCl, 2.5 mM KCl, 10 mM $MgCl_2$, 10 mM $MgSO_4$ and 20 mM glucose. The suspension is shaked for 1 h at 37° C. and 100 µl of the suspension is plated on LB plates containing 150 mg/l ampicillin for maintenance of the plasmid pQE_noNco.

Cells of *Escherichia coli* XL1-Blue harboring the vector pQE_noNco, are grown overnight in LB medium containing 180 mg/l of ampicillin for maintenance of the plasmid in the host cells. 7 ml of the culture are centrifuged for 20 min at 5,000 rpm. The cell pellet is used for isolation of the plasmid pQE_noNco with the mini plasmid isolation kit from Qiagen (Hilden, Germany). The pellet is resuspended in 0.3 ml of 10 mM EDTA in 50 mM tris hydrochloride, pH 8.0. 30 µg RNase A are added. 0.3 ml of 1% (w/v) SDS in 200 mM sodium hydroxide are added and incubated for 5 min at room temperature. 0.3 ml of chilled 3.0 M sodium acetate, pH 5.5 are added and incubated for 10 min on ice. The mixture is centrifuged for 15 min at 14,000 rpm in a minifuge. The supernatant is applied onto a Qiagen-tip 20, which is previously equilibrated with 1 ml of 750 mM NaCl, 15% (v/v) ethanol and 0.15% (v/v) Triton X-100 in 50 mM MOPS, pH 7.0. The Qiagen-tip is washed four times with 1 ml of 1000 mM NaCl and 15% (v/v) ethanol in 50 mM MOPS, pH 7.0. The DNA is eluted with 0.8 ml of 1250 mM NaCl and 15% (v/v) ethanol in 50 mM tris hydrochloride, pH 8.5. The DNA is precipitated with 0.56 ml of isopropanol, centrifuged 30 min at 14,000 rpm and washed with 1 ml of ice-cold 70% (v/v) ethanol. After drying in a speedvac for 5 min, the DNA is dissolved in 50 µl of redistilled $H_2O$. The solution contained 8.3 µg of the vector DNA pQE_noNco.

The DNA of the vector pQE_noNco is sequenced by the automated dideoxynucleotide method (Sanger et al. Proc. Natl. Acad. Sci. USA 74, 5463–5468 (1977)) using an ABI Prism 377™ DNA sequencer from Perkin Elmer (Norwalk, USA) with the ABI Prism™ Sequencing Analysis Software from Applied Biosystems Divisions (Foster City, USA).

The DNA sequence is found to be as expected.

2.0 µg of the vector pQE_noNco is digested with 30 U of EcoRI and 30 U of SalI (NEB) in a total volume of 60 µl containing 6 µl of EcoRI buffer (NEB). The reaction mix is incubated for 3 h at 37° C. The vector DNA is purified using the PCR purification kit from Qiagen.

25 pmol of the oligonucleotides 5'-CACACAGAAT-TCATTAAAGAG GAGAAATTAA CCATGGGAGGATC-CGTCGACCTGCAGCC-3' and 5'-GGCTGCAGGTC-GACGGA TCCTCCCATGGTTAATTTCTCCTCTTTA ATGAATTCTGTGTG-3' are dissolved in 6 µl EcoRI buffer (NEB) and 54 µl $H_2O$. The solution is heated at 96° C. for 2 min and cooled down to 10° C. within 12 h in order to hybridize the DNA linker. The reaction mix is supplied with 30 U of EcoRI and 30 U of SalI (NEB) and incubated for 3 h at 37° C. The reaction mix is heated to 65° C. for 30 min in order to inactivate the enzymes and cooled down to 10° C. within 12 h for hybridisation. The reaction mix contains approximately 730 ng of the DNA linker.

20 ng of the digested pQE_noNco vector DNA (see above) and 300 pg of the DNA linker, 2 µl of T4-Ligase buffer (Gibco-BRL) are ligated together with 1 U of T4-Ligase from Gibco-BRL (Eggenstein, Germany),), 2 µl of T4-Ligase buffer (Gibco-BRL) in a total volume of 10 µl yielding the plasmid pNCO113. The ligation mixture is incubated overnight at 4° C. With 2 µl of the ligation mixture electrocompetent *E. coli* XL1-Blue cells are transformed.

5 µg of the plasmid pNCO113 are isolated and the DNA sequence of the vector pNCO113 is sequenced as described above. The culture is on deposit with ATCC as a patent deposit with the title *Escherichia coli* strain XL1-Blue habouring plasmid pNCO113, assigned PTA-852, date of deposit: Oct. 14, 1999.

REFERENCE EXAMPLE 2

Production of an Expression Clone and Construction of an Expression Vector for 1-deoxy-D-xylulose 5-phosphate Synthase of *Bacillus subtilis*.

The expression vector pNCO113 is isolated as described in reference example 1. Chromosomal DNA from *Bacillus subtilis* strain BR151 (Williams et al. J. Bacteriol. 146(3), 1162–1165 (1981)) is isolated according to a method described in reference example 8.

The putative ORF yqiE coding for 1-deoxy-D-xylulose 5-phosphate synthase of *B. subtilis* (accession no. dbj D84432) from basepair (bp) position 193991 to 195892 is amplified by PCR using chromosomal *B. subtilis* DNA as template. The reaction mixture contained 25 pmol of primer TGATCCGCCATGGATCTTTTATCAATACAGG, 25 pmol of primer TTGAATAGAGGATCCCCGCC, 20 ng of chromosomal DNA, 2U of Taq DNA polymerase (Eurogentec, Seraing, Belgium) and 20 nmol of dNTPs in a total volume of 1.5 mM $MgCl_2$, 50 mM KCl, 10 mM tris hydrochloride, pH 8.8 and 0.1% (w/w) Triton X-100 in a total volume of 100 µl.

The mixture is denaturated for 3 min at 95° C. Then 30 PCR cycles for 60 sec at 94° C., 60 sec at 50° C. and 120 sec at 72° C. follow. After further incubation for 20 min at 72° C., the mixture is cooled to 4° C. An aliquot of 2 µl is subjected to agarose gel electrophoresis. The PCR amplificate is purified with the PCR purification kit from Qiagen. 500 µl of buffer PB (Qiagen) are added to 98 µl of PCR reaction mixture and applied to a Qiaquick column and centrifuged for 1 min at 14,000 rpm. The flow through is discarded. 0.75 ml of buffer PE (Qiagen) are loaded on the column and centrifuged as before. The flow through is discarded and the column is centrifuged for an additional 1 min at 14,000 rpm. The column is placed in a clean 1.5 ml eppendorf tube. 50 µl of H$_2$O (redistilled, sterile) are added to the column and it is centrifuged for 1 min at 14,000 rpm. The flow through contained 1.8 µg of purified PCR product.

2.0 µg of the vector pNCO113 and 1.8 µg of the purified PCR product are digested in order to produce DNA fragments with overlapping ends. Each restriction mixture contained 7 µl of SalI buffer from (NEB), 7 µg of BSA (NEB), 40 U of NcoI (NEB), 30 U of SalI (NEB) in a total volume of 70 µl and is incubated for 3 h at 37° C. Digested vector DNA and PCR product are purified using the PCR purification kit from Qiagen.

20 ng of vector DNA and 34 ng of PCR product are ligated together with 1 U of T4-Ligase from Gibco-BRL (Eggenstein, Germany), 2 µl of T4-Ligase buffer (Gibco-BRL) in a total volume of 10 µl yielding the plasmid pNCODXS-BACSU. The ligation mixture is incubated overnight at 4° C. With 2 µl of the ligation mixture electrocompetent *E. coli* XL1-Blue cells are transformed as described in example 2.6 µg of plasmid DNA pNCODXSBACSU were isolated.

The DNA insert of the plasmid pNCODXSBACSU is sequenced as described in reference example 1. The sequence is identical with the sequence found in the database (accession no. dbj D84432).

REFERENCE EXAMPLE 3

Preparation and Purification of Recombinant 1-deoxy-D-xylulose 5-phosphate Synthase of *B. subtilis*.

*E. coli* XL1-Blue cells harboring the plasmid pNCODX-SBACSU are grown, induced, harvested and stored as described in reference example 9.

2 g of the cells are thawed in 10 ml of 25 mM tris-HCl pH 8.0 containing 1 mM dithioerythritol, 10 mM EDTA and 6 mM phenylmethlysulfonyl fluoride in the presence of 1 mg lysozyme. The mixture is incubated at 37° C. for 0.5 h, cooled on ice and sonified 6×10 sec with a Branson Sonifier 250 (Branson SONIC Power Company, Danbury, USA), control value of 4 output. The suspension is centrifuged at 15,000 rpm at 4° C. for 30 min. The supernatant is applied on a column of Sepharose QFF (26 cm$^3$, Amersham Pharmacia Biotech, Freiburg, Germany) previously equilibrated with 200 ml 25 mM tris-HCl pH 8.0 containing 0.5 mM MgCl$_2$ and 0.03% sodium azide (buffer A). The column is washed with 60 ml buffer A monitoring the extinction at 280 nm. 1-deoxy-D-xylulose 5-phosphate synthase is eluted from the column with a gradient from 0–1 M sodium chloride in 300 ml of buffer A. The enzyme is identified by SDS-PAGE showing a band at 68 kDa. Fractions showing this protein band are collected and dialysed against buffer A overnight.

The enzyme is further purified on a column of hydroxyl apatite (Macro pep 40 µm (size 2.5×6 cm, Biorad, Munich, Germany) equilibrated with buffer A. The enzyme is eluted by a gradient of 0–1 M potassium phosphate, pH 6.5. The homogeneity of 1-deoxy-D-xylulose 5-phosphate synthase is judged by SDS-PAGE. A prominent band at 67 kDa is visible, which is in agreement to the calculated molecular mass. The yield of pure 1-deoxy-D-xylulose 5-phosphate synthase is 44 mg.

REFERENCE EXAMPLE 4

Determination of 1-deoxy-D-xylulose 5-phosphate Synthase Activity

1. By Nuclear Magnetic Resonance (NMR)

The assay mixture contains 400 mM tris hydrochloride pH 8.0, 25 mM [2-$^{13}$C]-sodium pyruvate, 50 mM D,L-glyceraldehyde 3-phosphate, 10 mM MgCl$_2$, 2 mM thiamine pyrophosphate, 1 mM dithiothreitol, 0.5 mM EDTA, 10% D$_2$O and 0.8 mg enzyme sample in a total volume of 0.5 ml. The mixture is incubated 3 h at 37° C. Protein is precipitated by the addition of 0.1 ml 50% trichloroacetic acid (TCA). After centrifugation a $^{13}$C-NMR-spectrum (62.9 Mhz, Bruker, Karlsruhe, Germany) is recorded. The turnover is calculated by integration of the 2C-signals of pyruvate and 1-deoxy-D-xylulose 5-phosphate. Pyruvate displays a 2C-signal at 196.5 ppm and a signal at 92.7 ppm which is assigned to the corresponding hydrate. 1-Deoxy-D-xylulose 5-phosphate displays a signal at 212.5 ppm.

2. By Photometric Detection (Variant A)

The assay mixture contains 200 mM tris hydrochloride pH 8.0, 25 mM sodium pyruvate, 50 mM D,L-glyceraldehyde 3-phosphate (previously neutralized with NaOH), 10 mM MgCl$_2$, 4 mM thiamine pyrophosphate, 8 mM dithiothreitol and 0.02 mg enzyme sample in a total volume of 25 ml. The mixture is incubated 20 min at 37° C. 25 µl of 30% TCA are added. The supernatant is added to a buffer containing 200 mM tris hydrochloride pH 8.0, 1 mM MnSO$_4$, 0.5 mM NADPH in a total volume of 0.95 ml. The extinction at 340 nm is determined. A solution (50 ml, 0.1 U) of 1-deoxy-D-xylulose 5-phosphate reductoisomerase is added and the mixture is incubated 30 min at 37° C. The extinction at 340 nm is determined again. The extinction difference is equivalent to the amount of consumed NADPH ($\epsilon_{340}$=6300 M$^{-1}$ cm$^{-1}$) which is equivalent to the amount of 1-deoxy-D-xylulose 5-phosphate produced.

3. By Photometric Detection (Variant B)

The assay mixture contains 200 mM tris hydrochloride pH 8.0, 5 mM sodium pyruvate, 10 mM D,L-glyceraldehyde 3-phosphate, 1 mM MnSO$_4$, 1 mM thiamine pyrophosphate, 1 mM dithiothreitol, 0.5 mM NADPH and 1 U of 1-deoxy-D-xylulose 5-phosphate reductoisomerase in a total volume of 1 ml. The mixture is incubated at 37° C. in a thermostated cuvette and the extinction at 340 nm is monitored. The assay is started by the addition of 5 µl enzyme sample. The negative slope of the extinction is equivalent to the rate of the 1-deoxy-D-xylulose 5-phosphate synthase reaction.

REFERENCE EXAMPLE 5

Production of an Expression Clone and Construction of an Expression Vector for 1-Deoxy-D-xylulose 5-Phosphate Reductoisomerase of *E. coli*

The *E. coli* ORF yaeM (accession no. gb AE000126) from bp position 9887 to 11083 is amplified by PCR using chromosomal *E. coli* DNA as template. Chromosomal DNA from *Escherichia coil* strain XL1-Blue is isolated according to a method described in reference example 8.

The reaction mixture contained 25 pmol of primer GGAGGATCCA TGAAGCAACTCACC, 25 pmol of primer GCGCGACTCTCTGCAGCCGG, 20 ng of chromosomal DNA, 2 U of Taq DNA polymerase (Eurogentec, Seraing, Belgium) and 20 nmol of dNTPs in a total volume of 100 µl of 1.5 mM $MgCl_2$, 50 mM KCl, 10 mM tris hydrochloride, pH 8.8 and 0.1% (w/w) Triton X-100.

The mixture is denatured for 3 min at 94° C. Then, 30 PCR cycles for 45 sec at 94° C., 45 sec at 50° C. and 75 sec at 72° C. follow. After further incubation for 7 min at 72° C., the mixture is cooled to 4° C. An aliquot of 2 µl is subjected to agarose gel electrophoresis.

The PCR amplificates are purified with a PCR purification kit from Qiagen as described in reference example 1.

2.5 µg of the vector pQE30 (Qiagen), isolated as described in reference example 1, and 2.0 µg of the purified PCR product are digested in order to produce DNA fragments with overlapping ends. Each restriction mixture contains 7 µl of NEB3 buffer, 50 U of BamHI (NEB), 40 U of PstI (NEB) in a total volume of 70 µl and is incubated for 3 h at 37° C. Digested vector DNA and PCR product are purified using the PCR purification kit from Qiagen as described in reference example 1.

20 ng of vector DNA and 22 ng of PCR product are ligated together with 1 U of T4-Ligase (Gibco), 2 µl of T4-Ligase buffer (Gibco) in a total volume of 10 µl, yielding the plasmid pQEyaeM. The ligation mixture is incubated overnight at 4° C. Each 2 µl of the ligation mixture is used for transforming electrocompetent *E. coli* XL1-Blue and M15 [pREP4] (Zamenhof et al., J. Bacteriol. 110, 171–178 (1972)) cells as described in reference example 1. The electrocompetent cells are prepared as described in reference example 1.

12 µg DNA of plasmid pQEyaeM are obtained.

The DNA insert of the plasmid pQEyaeM is sequenced as described in reference example 1 and is identical with the sequence in the database (accession no. gb AE000126).

REFERENCE EXAMPLE 6

Preparation and Purification of Recombinant 1-deoxy-D-xylulose 5-phosphate Reductoisomerase of *E. coli*.

Recombinant M15[pREP4] cells of *E. coli* containing overexpressed 1-deoxy-D-xylulose 5-phosphate reductoisomerase of *E. coli* are prepared identically to the preparation of reference example 9. The cells are thawed in 20 ml of 20 mM imidazole in 100 mM tris hydrochloride pH 8.0 and 0.5 M sodium chloride (standard buffer) in the presence of 1 mg/ml lysozyme and 100 µg/ml DNaseI. The mixture is incubated at 37° C. for 30 min, cooled on ice and sonified 6×10 sec with a Branson Sonifier 250 (Branson SONIC Power Company) set to 70% duty cycle output, control value of 4 output. The suspension is centrifuged at 15,000 rpm at 4° C. for 30 min. The cell free extract of recombinant 1-deoxy-D-xylulose 5-phosphate reductoisomerase of *E. coli* is applied on a column of $Ni^{2+}$-chelating sepharose FF (column volume 25 ml, Amersham Pharmacia Biotech) previously equilibrated with 20 mM imidazole in standard buffer. The column is washed with 100 ml of starting buffer. 1-Deoxy-D-xylulose 5-phosphate reductoisomerase is eluted with a linear gradient of 20–500 mM imidazole in standard buffer. 1-Deoxy-D-xylulose 5-phosphate reductoisomerase containing fractions are combined according to SDS-PAGE and dialysed overnight against 100 mM tris hydrochloride pH 8.0. The dialysed 1-deoxy-D-xylulose 5-phosphate reductoisomerase is concentrated by ultrafiltration (MWCO 10 kDa, Amicon, USA.) and applied on a Superdex 75 HR 26/60 column (Amersham Pharmacia Biotech). The homogeneity of 1-deoxy-D-xylulose 5-phosphate reductoisomerase is judged by SDS-PAGE. One band at 43 kDa is visible, which is in line with the calculated molecular mass. The yield of pure 1-deoxy-D-xylulose 5-phosphate reductoisomerase is 60 mg.

REFERENCE EXAMPLE 7

Determination of 1-deoxy-D-xylulose 5-phosphate Reductoisomerase Activity

Assay mixtures contain 100 mM tris hydrochloride pH 8.0, 1 mM $MnCl_2$, 0.5 mM NADPH and 5 µg enzyme sample in a total volume of 1 ml. The mixture is incubated at 37° C. in a thermostated cuvette and the reaction is monitored spectrophotometrically at 340 nm. The assay is started by the addition of 10 µl of 50 mM 1-deoxy-D-xylulose 5-phosphate. The negative slope of the extinction is equivalent to the rate of the reaction catalyzed by 1-deoxy-D-xylulose 5-phosphate reductoisomerase.

REFERENCE EXAMPLE 8

Production of an Expression Clone and Construction of an Expression Vector for ygbP of *E. coli*

Cells of *Escherichia coli* XL1-Blue harboring the expression vector pNCO113, are grown overnight in Luria Bertani (LB) medium containing 180 mg/l of ampicillin for maintenance of the plasmid in the host cells. 7 ml of the culture are centrifuged for 20 min at 5,000 rpm. The cell pellet is used for isolation of the plasmid pNCO113 with the mini plasmid isolation kit from Qiagen (Hilden, Germany). The pellet is resuspended in 0.3 ml of 10 mM EDTA in 50 mM tris hydrochloride, pH 8.0. 30 µg RNase are added. 0.3 ml of 1% (w/v) SDS in 200 mM sodium hydroxide are added and incubated for 5 min at room temperature. 0.3 ml of chilled 3.0 M sodium acetate, pH 5.5 are added and incubated for 10 min on ice. The mixture is centrifuged for 15 min at 14,000 rpm in a minifuge. The supernatant is applied onto a Qiagen-tip 20, which is previously equilibrated with 1 ml of 750 mM NaCl, 15% (v/v) ethanol and 0.15% (v/v) Triton X-100 in 50 mM MOPS, pH 7.0. The Qiagen-tip is washed four times with 1 ml of 1000 mM NaCl and 15% (v/v) ethanol in 50 mM MOPS, pH 7.0. The DNA is eluted with 0.8 ml of 1250 mM NaCl and 15% (v/v) ethanol in 50 mM tris hydrochloride, pH 8.5. The DNA is precipitated with 0.56 ml of isopropanol, centrifuged for 30 min at 14,000 rpm and washed with 1 ml of ice-cold 70% (v/v) ethanol. After drying in a speedvac for 5 min, the DNA is dissolved in 50 µl of redistilled $H_2O$. The solution contained 8.3 µg of DNA.

Chromosomal DNA from *Escherichia coli* strain XL1-Blue is isolated according to a method described by Meade, et al. (J. Bacteriol. 149, 114–122 (1982)). The *E. coli*. ORF ygbP (accession no. gb AE000358) from basepair (bp) position 6754 to 7464 is amplified by PCR using chromosomal *E. coli* DNA as template. The reaction mixture contained 25 pmol of primer AAATTAACCATGGCAACCACTCAT TTGG, 25 pmol of primer TTGGGCCTGCAGCGCCAAAGG, 20 ng of chromosomal DNA, 2 U of Taq DNA polymerase (Eurogentec, Seraing, Belgium) and 20 nmol of dNTPs in 1.5 mM $MgCl_2$, 50 mM KCl, 10 mM tris hydrochloride pH 8.8 and 0.1% (w/w) Triton X-100 in a total volume of 100 µl.

The mixture is denatured for 3 min at 95° C. Then 25 PCR cycles for 30 sec at 94° C., 30 sec at 50° C. and 45 sec at 72° C. follow. After further incubation for 7 min at 72° C., the mixture is cooled to 4° C. An aliquot of 2 µl is subjected to agarose gel electrophoresis. The PCR amplificate is purified with the PCR purification kit from Qiagen. 500 µl of buffer PB (Qiagen) are added to 98 µl of PCR reaction mixture and applied to a Qiaquick column and centrifuged for 1 min at 14,000 rpm. The flow through is discarded. 0.75 ml of buffer PE (Qiagen) are loaded on the column and centrifuged as before. The flow through is discarded and the column is centrifuged for an additional 1 min at 14,000 rpm. The column is placed in a clean 1.5 ml eppendorf tube. 50 µl of H$_2$O (redistilled, sterile) are added to the column and it is centrifuged for 1 min at 14,000 rpm. The flow through contained 1.5 µg of purified PCR product.

2.0 µg of the vector pNCO113 and 1.5 µg of the purified PCR product are digested in order to produce DNA fragments with overlapping ends. Each restriction mixture contained 7 µl of NEB3 buffer (NEB), 7 µg of BSA, 40 U of NcoI (NEB), 30 U of PstI (NEB) in a total volume of 70 µl and is incubated for 3 h at 37° C. Digested vector DNA and PCR product are purified using the PCR purification kit from Qiagen.

20 ng of vector DNA and 16 ng of PCR product are ligated together with 1 U of T4-Ligase from Gibco-BRL (Eggenstein, Germany), 2 µl of T4-Ligase buffer (Gibco) in a total volume of 10 µl yielding the plasmid pNCOygbP. The ligation mixture is incubated overnight at 4° C. With 2 µl of the ligation mixture electrocompetent *E. coli* XL1-Blue cells are transformed.

The plasmid pNCOygbP is isolated as described in reference example 1.

The DNA insert of the plasmid pNCOygbP is sequenced as described in reference example 1.

REFERENCE EXAMPLE 9

Preparation and Purification of Recombinant YgbP Protein of *E. coli*

0.5 liter of Luria Bertani (LB) medium containing 90 mg of ampicillin are inoculated with 10 ml of an overnight culture of *E. coli* strain XL1-Blue harboring plasmid pNCOygbP. The culture is grown in a shaking culture at 37° C. At an optical density (600 nm) of 0.7, the culture is induced with 2 mM IPTG. The culture is grown for further 5 h. The cells are harvested by centrifugation for 20 min at 5,000 rpm and 4° C. The cells are washed with 50 mM tris hydrochloride pH 8.0, centrifuged as above and frozen at −20° C. for storage.

The cells are thawed in 10 ml of 20 mM tris hydrochloride pH 8.0 containing 1 mM dithioerythritol, 0.02% sodium azide (buffer A) in the presence of 4 mg/ml lysozyme and 10 µg/ml DnaseI. The mixture is incubated at 37° C. for 1 h, cooled on ice and sonified 6×10 sec with a Branson Sonifier 250 (Branson SONIC Power Company, Danbury, USA) set to 70% duty cycle output, control value of 4 output. The suspension is centrifuged at 15,000 rpm at 4° C. for 30 min. The supernatant is applied on a column of Sepharose Q FF (size 4.6×24 cm, Amersham Pharmacia Biotech, Freiburg, Germany) previously equilibrated with 200 ml buffer A. The column is washed with buffer A monitoring at 280 nm. 4-Diphosphocytidyl-2C-methyl-D-erythritol synthase is eluted from the column with a gradient from 0–0.5 M sodium chloride in 300 ml of buffer A. The enzyme is identified by SDS-PAGE showing a band at 26 kDa. Fractions showing this protein band are collected and dialysed against buffer A overnight. The enzyme is further purified on a column of Red Sepharose CL-6B (size 2.6×10 cm, Amersham Pharmacia Biotech) equilibrated with buffer A. The enzyme is passed through the column and is loaded on a Source 15Q (column volume 20 ml, Amersham Pharmacia Biotech). The enzyme is eluted by a gradient of 0–0.5 M sodium chloride in 250 ml buffer A. The homogeneity of 4-diphosphocytidyl-2C-methyl-D-erythritol synthase is judged by SDS-PAGE.

REFERENCE EXAMPLE 10

Enzymatic Production of 4-diphosphocytidyl-2C-methyl-D-erythritol

A solution containing 100 mM tris HCl pH 8.0, 10 mM MgCl$_2$, 10 mM CTP, 0.12 µCi of [2-$^{14}$C]2C-methyl-D-erythritol 4-phosphate, 46 mM of 2C-methylerythritol 4-phosphate and 225 µg of YgbP protein from recombinant *E. coli* is incubated at 37° C. for 1 h. The reaction is monitored by $^{31}$P-NMR. The product displaying two $^{31}$P-NMR dubletts at −7.2 ppm and −7.8 ppm is purified by HPLC on a column of the anionic exchanger Nucleosil 10SB (4.6×250 mm) using 0.1 M ammonium formate in 40% (v/v) methanol as eluent at a flow rate of 1 ml/min. The eluent is monitored by a UV-diode array detector (J&M TIDAS) and a radiomonitor from Berthoid. 4-Diphosphocytidyl-2C-methyl-D-erythritol is eluted at 30 ml. The fraction containing 4-diphosphocytidyl-2C-methyl-D-erythritol is collected and lyophylized. The residue is dissolved in 0.5 ml of deuterated water and subjected to NMR analysis.

REFERENCE EXAMPLE 11

Production of an Expression Clone and Construction of an Expression Vector for ychB of *E. coli*

Chromosomal DNA from *E. coli* strain XL1-Blue is isolated as described in reference example 8.

The *E. coli* ORF ychB (accession no. gb AE000219) from basepair (bp) position 5720 to 6571 is amplified by PCR using chromosomal *E. coli* DNA as template. The reaction mixture contained 25 pmol of primer 5'-GAGGAGAAAT-TAACCATGCGGACACAGTGGCC-3', 25 pmol of primer 5'-GTCACCGAACTGCAGCTTGCCCG-3', 20 ng of chromosomal DNA, 2 U of Taq DNA polymerase (Eurogentec, Seraing, Belgium) and 20 nmol of dNTPs in of 1.5 mM MgCl$_2$, 50 mM KCl, 10 mM tris hydrochloride pH 8.8 and 0.1% (w/w) Triton X-100 in a total volume of 100 µl.

The mixture is denaturated for 3 min at 95° C. Then 25 PCR cycles for 30 sec at 94° C., 30 sec at 50° C. and 45 sec at 72° C. follow. After further incubation for 7 min at 72° C., the mixture is cooled to 4° C. An aliquot of 2 µl is subjected to agarose gel electrophoresis. The PCR amplificate is purified with PCR purification kit from Qiagen. 1.5 µg of purified PCR product are obtained.

The PCR amplificate is used as template for a second PCR reaction. The reaction mixture contained 25 pmol of primer 5'-ACACAGAATTCATTAAAGAGGAGAAAT-TAACCATG-3', 25 pmol of primer GTCACCGAACTG-CAGCTTGCCCG-3', 2 µl of the first PCR amplification, 2 U of Taq DNA polymerase (Eurogentec, Seraing, Belgium) and 20 nmol of dNTPs in a total volume of 100 µl of 1.5 mM MgCl$_2$, 50 mM KCl, 10 mM tris hydrochloride, pH 8.8 and 0.1% (w/w) Triton X-100.

The mixture is denaturated for 3 min at 95° C. Then 40 PCR cycles for 45 sec at 94° C., 45 sec at 50° C. and 60 sec at 72° C. follow. After further incubation for 20 min at 72° C., the mixture is cooled to 4° C. An aliquot of 2 µl is subjected to agarose gel electrophoresis.

The PCR amplificate is purified with the PCR purification kit from Qiagen as described in reference example 1.

2.0 µg of the vector pNCO113 and 1.5 µg of the purified PCR product are digested in order to produce DNA fragments with overlapping ends. Each restriction mixture contained 6 µl of NEB3 buffer, 6 µg of BSA, 30 U of EcoRI (NEB), 30 U of PstI (NEB) in a total volume of 60 µl and is incubated for 3 h at 37° C. Digested vector DNA and PCR product are purified using the PCR purification kit from Qiagen.

20 ng of vector DNA and 18 ng of PCR product are ligated together with 1 U of T4-Ligase from Gibco-BRL (Eggenstein, Germany), 2 µl of T4-Ligase buffer (Gibco-BRL) in a total volume of 10 µl yielding the plasmid pNCOychB. The ligation mixture is incubated overnight at 4° C. With 2 µl of the ligation mixture electrocompetent E. coli XL1-Blue cells are transformed and 100 µl of the cell/DNA suspension is plated on LB plates containing 150 mg/l ampicillin for maintenance of the plasmid pNCOychB. The plasmid pNCOychB is isolated as described before. 9 µg of plasmid DNA are obtained.

The DNA insert of the plasmid pNCOychB is sequenced as described in reference example 1. The DNA sequence is found to be identical to the sequence in the data base (accession no. gb AE000219).

REFERENCE EXAMPLE 12

Preparation and Purification of Recombinant YchB Protein of E. coli 0.5 liter of LB medium containing 90 mg of ampicillin are inoculated with 10 ml of an overnight culture of E. coli strain XL1-Blue harboring plasmid pNCOychB.

The culture is grown in a shaking culture at 37° C. At an optical density (600 nm) of 0.7, the culture is induced with 2 mM IPTG. The culture is grown for further 5 h. The cells are harvested by centrifugation for 20 min at 5,000 rpm and 4° C. The cells are washed with 50 mM tris hydrochloride pH 8.0, centrifuged as above and frozen at −20° C. for storage.

The cells are thawed in 10 ml of 20 mM tris hydrochloride pH 8.0 containing 1 mM dithioerythritol, 0.02% sodium azide (buffer A) in the presence of 4 mg/ml lysozyme and 10 µg/ml DnaseI. The mixture is incubated at 37° C. for 1 h, cooled on ice and sonified 6×10 sec with a Branson Sonifier 250 (Branson SONIC Power Company, Danbury, USA) set to 70% duty cycle output, control value of 4 output. The suspension is centrifuged at 15,000 rpm at 4° C. for 30 min. The supernatant is applied on a column of Sepharose QFF (column volume 30 ml, Amersham Pharmacia Biotech, Freiburg, Germany) previously equilibrated with 150 ml buffer A. The column is washed with buffer A monitoring at 280 nm. YchB protein is eluted from the column with a gradient from 0–0.5 M sodium chloride in 150 ml of buffer A. The enzyme is identified by SDS-PAGE showing a band at 30 kDa. Fractions showing this protein band are collected and ammonium sulfate is added to a final concentration of 0.5 M. The enzyme is further purified on a column of Phenyl Sepharose 6FF (column volume 16 ml, Amersham Pharmacia Biotech) equilibrated with buffer A containing 0.5 M ammonium sulfate. Then the YchB protein is eluted by linear gradient from 0.5–0 M ammonium sulfate in 100 ml of buffer A. Fractions containing protein are pooled and concentrated to 3 ml by ultrafiltration (MWCO 10 kDa, Amicon, USA). Then the enzyme is further purified on Superdex 75 HR 26/60 equilibrated with buffer A in the presence of 100 mM sodium chloride. The YchB protein is eluted at 165 ml. The homogeneity of the YchB protein is judged by SDS-PAGE.

REFERENCE EXAMPLE 13

Enzymatic Preparation of 4-diphosphocytidyl-2C-methyl-D-erythritol 2-phosphate

A solution containing 5 mM [2-$^{14}$C]4-diphosphocytidyl-2C-methyl-D-erythritol (0.04 µCi/mmol), 5 mM ATP, 5 mM MgCl$_2$, 5 mM DTT, 100 µg of purified YchB protein and 100 mM tris hydrochloride pH 8.0 in a total volume of 4 ml is incubated for 2 h at 37° C. The reaction is monitored by $^{31}$P-NMR spectroscopy. Then the sample is centrifuged through a Nanosep 10K membrane (PALLGelmann, Robdorf, Germany). The product displaying $^{31}$P signals at 0.49, −7.28, and −8.00 ppm (referenced to external 85% phosphoric acid) is purified by HPLC on a column of the anionic exchanger Nucleosil 10SB (4.6×250 mm, Macherey-Nagel, Düren, Germany), equilibrated with 0.1 M ammonium formate in 40% (v/v) methanol at a flow rate of 1 ml/min. The HPLC system is equipped with a Wellchrom HPLC pump K-1001, a Wellchrom Spectro-Photometer K-2600 (Knauer, Berlin, Germany) and a radiomonitor (Berthold, Wildbad, Germany). After injection of the sample, the column is washed with 30 ml of 0.1 M ammonium formate in 40% (v/v) methanol. 4-Diphosphocytidyl-2C-methyl-D-erythritol 2-phosphate is eluted at 14 ml by a linear gradient from 0.1 M ammonium formate in 40% (v/v) methanol to 1 M ammonium formate in 0% (v/v) methanol in 30 ml. Fractions containing 4-diphosphocytidyl-2C-methyl-D-erythritol 2-phosphate are collected and lyophylized. The residue is dissolved in 0.5 ml of deuterated water and subjected to NMR analysis. The concentration of 4-diphosphocytidyl-2C-methyl-D-erythritol 2-phosphate is 21 mM.

REFERENCE EXAMPLE 14

Construction of an Expression Clone for ygbB from E. coli

The E. coli ORF ygbB (accession no. gb AE000358) from bp position 6231 to 6754 is amplified by PCR using chromosomal E. coli DNA as template. Chromosomal DNA from E. coli strain XL1-Blue is isolated as described in reference example 8.

The reaction mixture contained 10 pmol of primer GAGGAGAAATTAACCAT GCGAATTGGACACGGTTTTG, 10 pmol of primer TATTATCTGCAGCCTTG CGGTTTACCGTGGAGG, 20 ng of chromosomal DNA, 2 U of Taq DNA polymerase (Eurogentec, Seraing, Belgium) and 20 nmol of dNTPs in a total volume of 100 µl of 1.5 mM MgCl$_2$, 50 mM KCl, 10 mM tris hydrochloride, pH 8.8 and 0.1% (w/w) Triton X-100.

The mixture is denaturated for 5 min at 94° C. Then 30 PCR cycles for 30 sec at 94° C., 45 sec at 50° C. and 45 sec at 72° C. follow. After further incubation for 7 min at 72° C., the mixture is cooled to 4° C. An aliquot of 2 µl is subjected to agarose gel electrophoresis. The PCR amplificate is used as template for a second PCR reaction. The reaction mixture contained 50 pmol of primer ACACAGAATTCATTAAA-GAGGAGAAATTAACCATG, 50 pmol of primer TATTATCTGCAGCCTTGCGGTTTACCGTGGAGG, 2.5 µl of the first PCR amplification , 10 U of Taq DNA polymerase (Eurogentec, Seraing, Belgium) and 100 nmol of dNTPs in a total volume of 500 µl of 1.5 mM MgCl$_2$, 50 mM KCl, 10 mM tris hydrochloride, pH 8.8 and 0.1% (w/w) Triton X-100. The mixture is apportioned in 5 PCR-tubes.

The mixtures are denaturated for 5 min at 94° C. Then 25 PCR cycles for 30 sec at 94° C., 45 sec at 50° C. and 45 sec at 72° C. follow. After further incubation for 7 min at 72° C., the mixture is cooled to 4° C. An aliquot of 2 µl is subjected to a agarose gel electrophoresis.

The PCR amplificates are purified with a PCR purification kit from Qiagen as described in reference example 1.

4.5 µg of the vector pNCO113 (isolated as described in reference example 1) and 3.4 µg of the purified PCR product are digested in order to produce DNA fragments with overlapping ends. Each restriction mixture containes 20 µl of NEB3 buffer, 100 U of EcoRI (NEB), 100 U of PstI (NEB) in a total volume of 200 µl and is incubated for 3 h at 37° C. Digested vector DNA and PCR product are purified using the PCR purifiaction kit from Qiagen as described in reference example 1.

100 ng of vector DNA and 35 ng of PCR product are ligated together with 1 U of T4-Ligase (Gibco), 2 µl of T4-Ligase buffer (Gibco) in a total volume of 10 µl, yielding the plasmid pNCOygbB. The ligation mixture is incubated for 2 h at 25° C. 1 µl of the ligation mixture is transformed into electrocompetent E. coli XL1-Blue cells as described in reference example 1. The electrocompetent cells are prepared as described in reference example 1.

REFERENCE EXAMPLE 15

Preparation and Purification of Recombinant YgbB Protein of E. coli

The cell free extract of YgbB protein from E. coli is prepared identically to the preparation in reference example 9. The supernatant is applied on a column of Sepharose Q FF (column volume 30 ml, Amersham Pharmacia Biotech, Freiburg, Germany) previously equilibrated with 120 ml of buffer A. The column is washed with 90 ml of buffer A. Then the YgbB protein is eluted with a linear gradient of 0–0.5 M NaCl in 150 ml buffer A. The homogeneity of YgbB potein is judged by SDS-PAG E.

REFERENCE EXAMPLE 16

Production of an Expression Clone and Construction of an Expression Vector for a 6xHis-YgbB Fusion Protein of E. coli The E. coli ORF ygbB (accession no. gb AE000358) from bp position 6231 to 6754 is amplified by PCR using chromosomal E. coli DNA as template. Chromosomal DNA from E. coli strain XL1-Blue is isolated according to a method described in reference example 8.

The reaction mixture contained 10 pmol of primer GAGAAGGATCCATGCGAATTGGACACG-GTTTTGACG, 10 pmol of primer TATTATCTGCAGCCT-TGCGGTTTACCGTGGAGG, 20 ng of chromosomal DNA, 2 U of Taq DNA polymerase (Eurogentec, Seraing, Belgium) and 20 nmol of dNTPs in a total volume of 100 µl of 1.5 mM MgCl$_2$, 50 mM KCl, 10 mM tris hydrochloride, pH 8.8 and 0.1% (w/w) Triton X-100.

The mixture is denaturated for 5 min at 94° C. Then 30 PCR cycles for 30 sec at 94° C., 45 sec at 50° C. and 45 sec at 72° C. follow. After further incubation for 7 min at 72° C., the mixture is cooled to 4° C. An aliquot of 2 µl is subjected to agarose gel electrophoresis.

The PCR amplificate is purified with a PCR purification kit from Qiagen as described in reference example 1.

1.0 µg of the vector pQE30, isolated as described in reference example 1 (Qiagen) and 0.5 µg of the purified PCR product are digested in order to produce DNA fragments with overlapping ends. Each restriction mixture contains 10 µl of NEB3 buffer from NEB, 100 U of BamHI (NEB), 100 U of PstI (NEB) in a total volume of 100 µl and is incubated for 3 h at 37° C. Digested vector DNA and PCR product are purified using the PCR purifiaction kit from Qiagen as described in reference example 1.

5 fmol of vector DNA and 14 fmol of PCR product are ligated together with 1 U of T4-Ligase (Gibco), 2 µl of T4-Ligase buffer (Gibco) in a total volume of 10 µl, yielding the plasmid pQEygbB. The ligation mixture is incubated for 2 h at 25° C. 1 µl of the ligation mixture is transformed into electrocompetent E. coli XL1-Blue cells as described in reference example 1. The electrocompetent cells are prepared as described in reference example 1. The plasmid pQEygbB is isolated as described in reference example 1. 12 µg of plasmid DNA are obtained.

The DNA insert of the plasmid pQEygbB is sequenced as described in reference example 1 and is identical to the sequence in the database (accession no. gb AE000358). The 5'-end of the DNA insert carries the coding region for 6 histidine residues.

REFERENCE EXAMPLE 17

Preparation and Purification of Recombinant 6xHis-YgbB Fusion Protein of E. coli Recombinant XL1-Blue cells of E. coli containing overexpressed YgbB (N-terminal His-tagged) of E. coli are prepared as in reference example 9. The cells are thawed in 20 ml of 20 mM imidazole in 100 mM tris hydrochloride pH 8.0 and 0.5 M sodium chloride (standard buffer) in the presence of 1 mg/ml lysozyme and 100µg/ml DnaseI. The mixture is incubated at 37° C. for 30 min, cooled on ice and sonified 6×10 sec with a Branson Sonifier 250 (Branson SONIC Power Company) set to 70% duty cycle output, control value of 4 output. The suspension is centrifuged at 15,000 rpm at 4° C. for 30 min. The cell free extract of recombinant YgbB protein is applied on a column of Ni$^{2+}$-Chelating sepharose FF (column volume 25 ml, Amersham Pharmacia Biotech) previously equilibrated with 20 mM imidazole in standard buffer. The column is washed with 100 ml of starting buffer. YgbB protein is eluted with a linear gradient of 20–500 mM imidazole in standard buffer. YgbB protein-containing fractions are combined according to SDS-PAGE and dialysed overnight against 100 mM tris hydrochloride pH 8.0. The dialysed YgbB protein is concentrated by ultrafiltration (MWCO 10 kDa, Amicon, USA.) and applied on Superdex 75 HR 26/60 (Amersham Pharmacia Biotech). The homogeneity of YgbB protein is judged by SDS-PAGE. The objected band at 17 kDa is in agreement with the calculated molecular mass. 27 mg of pure enzyme were obtained.

REFERENCE EXAMPLE 18

Enzymatic Preparation of 2C-methyl-D-erythritol 2,4-cylopyrophosphate

A solution containing 5 mg [2-$^{14}$C]4-diphosphocytidyl-2C-methyl-D-erythritol (0.02 µCi/mmol), 5 mM MgCl$_2$, 5 mM ATP, 5 mM DDT, 100 µg purified YchB protein, 200 µg purified YgbB protein and 100 mM tris hydrochloride pH 8.0 in a total volume of 4 ml is incubated for 2 h at 37° C. The reaction is monitored by $^{13}$C- and $^{31}$P-NMR spectroscopy. The solution is passed through a Nanosep 10K membrane (PALLGemann, Roβdorf, Germany). The product displaying two 31P-NMR signals at −7.65 ppm and −11.66 ppm (dubletts, $^{31}$P-$^{31}$P coupling contstant, 23.6 Hz) and displaying two intense $^{13}$C-NMR signals at 83.87 ppm is purified by HPLC on a column of the anionic exchanger Nucleosil 10SB (4.6×250 mm, Macherey-Nagel, Düren, Germany) using 40% (v/v) methanol containing 0.1 M ammonium formate as eluent at a flow rate of 1 ml/min. 2C-methyl-D-erythritol 2,4-cyclopyrophosphate is eluted at 34 ml. Fractions containing 2C-methyl-D-erythritol 2,4-cyclopyrophosphate are collected and lyophylized. The residue is dissolved in 0.5 ml of deuterated water and subjected to NMR anylysis. The concentration of 2C-methyl-D-erythritol 2,4-cyclopyrophosphate is 18 mM.

REFERENCE EXAMPLE 19

Identification of 2C-methyl-D-erythritol 2,4-cyclopyrophosphate

The elucidation of the structure is performed with [2,2-methyl-$^{13}$C$_2$]2C-methyl-D-erythritol 2,4-cyclopyrophosphate (Table 6).

$^1$H-NMR and $^1$H-decoupled $^{13}$C-NMR spectra are recorded using a AVANCE DRX 500 spectrometer from Bruker (Karlsruhe, Germany). The frequencies are 500.1 MHZ and 125.6 Mhz for $^1$H and $^{13}$C, respectively. The chemical shifts are referenced to external trimethylsilylpropane sulfonate. $^{31}$P-NMR spectra are recorded using a AC 250 spectrometer from Bruker at a frequency of 101.3 MHz. The chemical shifts are referenced to external 85% H$_3$PO$_4$.

The structure of the product is evaluated by a multinuclear multidimensional NMR approach (Table 6). Specifically, the compound is characterized by two $^1$H decoupled $^{31}$P-NMR signals at −7.65 ppm (dublett with a $^{31}$P-$^{31}$P coupling constant of 23.6 Hz) and −11.66 ppm (double-double dublett with a $^{31}$P-$^{31}$P coupling constant of 23.6 Hz and a $^{31}$P-$^{13}$C coupling constant of 8.5 Hz, respectively). The $^{31}$P-NMR signal at 7.65 ppm is broadened without $^1$H decoupling. The detected $^{31}$P-NMR chemical shift range, as well as the $^{31}$P-$^{31}$P couplings implied that the unknown compound is a pyrophosphate. Moreover, the detected $^{31}$P-$^{13}$C couplings for the $^{31}$P-NMR signal at −11.66 ppm in conjunction with the missing $^{31}$P-$^1$H coupling for the signal indicate that one phosphate unit of the pyrophosphate moiety is connected to C-2 of 2C-methyl-D-erythritol. In line with this conclusion, $^{13}$C-$^{31}$P couplings are observed for the $^{13}$C-NMR signals reflecting C-2 and C-2-methyl.

In conjunction with the observed $^{13}$C-$^{13}$C couplings (Table 6), these data are the basis of the $^1$H- and $^{13}$C-NMR signal assignments. The $^{13}$C signal at 65.72 ppm (reflecting C-4) showed $^{13}$C-$^{31}$P coupling suggesting that the pyrophosphate motif is also connected to C-4. The $^{13}$C-NMR assignments are further confirmed by two-dimensional INADEQUATE experiments establishing the $^{13}$C-$^{13}$C connectivities.

In summary, the $^1$H-, $^{13}$C- and $^{31}$P-NMR data clearly established the product as 2C-methyl-D-erythritol 2,4-cyclopyrophosphate. The NMR data were in close correspondence to reported data for this compound (Ostrovsky et al. Biofactors 4 (1), 63–68 (1992); Turner et al. Biochem. J. 285, 387–390 (1992)).

TABLE 6

NMR data of [2,2-methyl-$^{13}$C$_2$]-2C-methyl-D-erythritol 2,4-cyclopyrophosphate

| | Chemical shifts, ppm | | | Coupling constants, Hz | | | | | |
|---|---|---|---|---|---|---|---|---|---|
| Position | $^1$H | $^{13}$C | $^{31}$P | $J_{PH}$ | $J_{PC}$ | $J_{PP}$ | $J_{CH}$ | $J_{CC}$ | $J_{HH}$ |
| 1 | 3.51 (dt, 1H)$^a$ | 66.95 (d)$^b$ | | | | | 1.7 | 41.8 (2) | 12.4 (1) |
| 1* | 3.66 (dd, 1H) | | | | | | 1.8 | | 12.4 (1) |
| 2 | | 83.87 (dd) | | | 8.4 | | | 39.8 (2-methyl) | |
| 2-methyl | 1.31 (dd, 3H) | 16.30 (dd) | | | 5.3 | | 128.4, 4.0 | 39.8 (2) | |
| 3 | 3.98 | 68.42 (dm) | | | n.d. | | | 46.0 (2) | n.d |
| 4 | | 65.72 (d) | | | 6.6 | | | | n.d. |
| 4* | 4.13 (m, 3H) | | | | | | | | n.d. |
| P (4) | | | −7.65 (d)$^c$ | n.d. | | 23.6 | | | |
| P (2) | | | −11.66 (ddd) | | 8.5, 5.3 | 23.6 | | | |

$^a$Referenced to external trimethylsilylpropane sulfonate. The multiplicities and the relative integral values of signals in the $^1$H-NMR spectrum are given in parentheses.
$^b$Referenced to external trimethylsilylpropane sulfonate. The multiplicities of the $^1$H decoupled $^{13}$C-NMR signals are given in parentheses.
$^c$Referenced to external 85% ortho-phosphoric acid. The multiplicities of the $^1$H decoupled $^{31}$P-NMR signals are given in parentheses.

REFERENCE EXAMPLE 20

Comprehensive Enzymatic Synthesis of 4-diphosphocytidyl-[2,2-methyl-$^{13}$C$_2$]-2C-methyl-D-erythritol Step a) Enzymatic Synthesis of [1,2-$^{13}$C$_2$]-1-deoxy-D-xylulose 5-phosphate.

Crude dihydroxyacetone phosphate is prepared as described by Effenberger and Straub (Tetrahedron Lett. 28, 1641–1644 (1987)). 1 g of dihydroxyacetone phosphate is dissolved in 70 ml of a solution of 57 mM [2,3-$^{13}$C$_2$]sodium pyruvate, 10 mM MgSO$_4$ and 2.5 mM thiaminepyrophosphate in 150 mM tris hydrochloride, pH 8.0. 17,000 U of triose phosphate isomerase (rabbit muscle) are added and the solution is incubated 105 min at 37° C. 0.774 ml (7.4 U) of recombinant 1-deoxyxylulose 5-phosphate synthase from *B. subtilis* are added. The reaction is monitored as described in reference example 4. After 8 h the reaction is stopped by adjusting the pH to a value of 3 by addition of 1 M HCl (11.2 ml). The reaction mixture is stored at −20° C.

Step b) Enzymatic Synthesis of [2,2-methyl-$^{13}C_2$]-2C-methyl-D-erythritol 4-phosphate.

To the reaction mixture obtained in step a, containing [1,2-$^{13}C_2$]-1-deoxy-D-xylulose 5-phosphate, 19 ml of 1 M tris buffer pH 8.0, 1.1 ml of 1 M MgCl$_2$ solution, 3 g glucose (72 mmol) and 6 ml of solution of 0.1 M MnCl$_2$ are added and the pH is adjusted to 8.0 with (7 ml 1 M NaOH). Precipitate is separated by centrifugation. To a final volume of 200 ml, water, 250 U of glucose dehydrogenase from *B. megaterium* and 56.6 mg NADP$^+$ (80 µmol) are added. After 5 min of preincubation at 37° C., 2 ml (11.2 U) of recombinant 1-deoxy-D-xylulose 5-phosphate reductoisomerase from *E. coli* are added. After ca. 30 h the reaction is stopped by the addition of 8 ml of 2 N HCl. The reaction mixture is stored at −20° C.

Step c) Enzymatic Synthesis of 4-diphosphocytidyl-[2,2-methyl-$^{13}C_2$]-2C-methyl-D-erythritol.

The pH of the reaction mixture obtained in step b, containing [2,2-methyl-$^{13}C_2$]-2C-methyl-D-erythritol 4-phosphate, is adjusted to 7.0 by addition of 4 ml 2 M NaOH. 1.4 g of CTP (2.5 mmol) is added and the pH is adjusted to 8.0 with 6 ml 2 N NaOH. After 5 min of preincubation at 37° C., 1.5 ml (51.8 U) of YgbP protein from *E. coli* solution are added. The reaction is monitored as described in reference example 10. After ca. 5 h the reaction mixture is purified and lyophylized as described in reference example 10. 550 mg of pure 4-diphosphocytidyl-[2,2-methyl-$^{13}C_2$]-2C-methyl-D-erythritol are obtained.

REFERENCE EXAMPLE 21

Enzymatic Synthesis of 4-diphosphocytidyl-[2,2-methyl-$^{13}C_2$]-2C-methyl-D-erythritol in a One-Vial Reaction A reaction mixture containing 3 g glucose, 1 g of dihydroxyacetone phosphate (5.7 mmol), 1.4 g of CTP (2.5 mmol), 0.45 g of 2,3-$^{13}C_2$-sodium pyruvate (4 mmol), 56.6 mg NADP$^+$(80 µmol), in 150 mM tris hydrochloride, pH 8.0 is prepared. 17,000 U of triose phosphate isomerase, 250 U of glucose dehydrogenase, 7 U of 1-deoxyxylulose 5-phosphate synthase, 13 U of 1-deoxy-D-xylulose 5-phosphate reductoisomerase and 55 U of YgbP protein are added.

To a final volume of 200 ml, 10 mM MgCl$_2$, 10 mM MnSO$_4$, 2.5 mM thiamine pyrophosphate in 150 mM tris hydrochloride, pH 8.0 are added. The pH is adjusted to 8.0 with 5 ml 1 M NaOH. The reaction mixture is incubated at 37° C. The reaction is monitored as described in reference example 10. After 30 h the reaction mixture is purified and lyophylized as described in reference example 10. 490 mg of pure 4-diphosphocytidyl-[2,2-methyl-$^{13}C_2$]-methyl-D-erythritol are obtained.

REFERENCE EXAMPLE 22

Large Scale Preparation of 2C-methyl-D-erythritol 4-phosphate

This preparation can be performed with any $^{13}C$-labeled sample of glucose or pyruvate as starting materials. In this example, it is described for [U-$^{13}C_6$]-glucose and [2,3-$^{13}C_2$]-pyruvate.

Step a) Preparative Synthesis of [U-$^{13}C_5$]-1-deoxy-D-xylulose 5-phosphate.

A reaction mixture containing 166 mg [U-$^{13}C_6$]-glucose (0.89 mmol), 44 mg thiamine pyrophosphate, 1.02 g of ATP (1.79 mmol), 200 mg of [2,3-$^{13}C_2$]-pyruvate (1.79 mmol), 6 mM MgCl$_2$ in 150 mM tris hydrochloride, pH 8.0 is prepared. 410 U of triose phosphate isomerase (from rabbit muscle, Type III-S, E. C. 5.3.1.1., Sigma), 360 U hexokinase (from Bakers Yeast, Type VI, E. C. 2.7.1.1, Sigma), 50 U phosphoglucose isomerase (from Bakers Yeast, Type III, E. C. 5.3.1.9, Sigma), 20 U phosphofructokinase (from *Bacillus stearothermophilus*, Type VII, E. C. 2.7.1.11, Sigma), 35 U aldolase (from rabbit muscle, E C. 4.1.2.13, Sigma) and 2 U recombinant DXP synthase from *B. subtilis* are added to a final volume of 58 ml. The reaction mixture is incubated at 37° C. overnight. During the reaction, the pH is held at a constant value of 8.0 by the addition of 1 M NaOH (2 ml). The reaction is stopped by adding 3 ml of 2 N hydrochloric acid. $^{13}C$-NMR-spectra are recorded for monitoring the conversion (Table 7).

TABLE 7

NMR data of [U-$^{13}C_5$]-1-deoxy-D-xylulose 5-phosphate

| Position | Chemical shifts, ppm$^a$ | Coupling constants, Hz | |
|---|---|---|---|
| | $^{13}C$ | $J_{PC}$ | $J_{CC}$ |
| 1 | 25.9 | | 41.1 (2), 12.8 (3) |
| 2 | 213.1 | | 41.3 (1), 41.3 (3), 3.1 (5) |
| 3 | 77.0 | | 41.5 (2), 40.2 (4), 12.8 (1) |
| 4 | 70.7 | 6.9 | 43.2 (5), 39.6 (3) |
| 5 | 64.3 | 4.6 | 43.4 (4), 3.1 (2) |

$^a$Referenced to external trimethylsilylpropane sulfonate.

Step b) Preparative Synthesis of [U-$^{13}C_5$]-2C-methyl-D-erythritol 4-phosphate.

To the solution of step a) 10 U DXP reductoisomerase, 120 U glucose dehydrogenase (from *Bacillus megaterium*, E. C. 1.1.1.47, Sigma), 0.97 g glucose, 200 mM MgCl$_2$ and 0.3 mM NADP$^+$ are added. The pH is adjusted to 8.0 with 1.5 ml of 4 N sodium hydroxide. After centrifugation the volume is 72 ml. The reaction mixture is incubated at 37° C. overnight. The conversion is monitored by recording $^{13}C$-NMR-spectra of the accumulating product (Table 8). The reaction product is purified by HPLC on a column of the anionic exchanger Nucleosil 10 SB (16×250 mm) using 0.5 M formic acid as eluent at a flow rate of 13 ml/min. The eluent is monitored by a refractometer (GAT-LCD210 from Gamma Analyse Technik, Bremerhafen, Germany). The product is eluted at 14.5 min. The fraction containing [U-$^{13}C_5$]-2C-methyl-D-erythritol 4-phosphate is collected and lyophylized. The amount is 86 mg.

TABLE 8

NMR data of [U-$^{13}C_5$]-2C-methyl-D-erythritol

| Position | Chemical shifts, ppm$^a$ |
|---|---|
| 1 | 66.5 |
| 2 | 74.1 |
| 2-Methyl | 18.5 |
| 3 | 74.1 |
| 4 | 64.6 |

$^a$Referenced to external trimethylsilylpropane sulfonate.

REFERENCE EXAMPLE 23

Enzymatic Synthesis of 4-diphosphocytidyl-2C-methyl-D-erythritol 2-phosphate

This preparation can be performed with any $^{13}C$-labeled sample of 2C-methyl-D-erythritol 4-phosphate as starting material. In this example it is described for [1,3,4-$^{13}C_3$]-2C-methyl-D-erythritol 4-phosphate.

To a reaction mixture containing 15 mg of purified [1,3,4-$^{13}C_3$]-2C-methyl-D-erythritol 4-phosphate (69 µmol), 34 mg CTP (69 µmol), 16 mg sodium phosphoenol pyruvate (69 µmol), 1.9 mg ATP (3.5 µmol), 10 mg $MgCl_2$, 5 mM DTT, 10 mM KCl and 150 mM tris hydrochloride, pH 8.0, 60 µl of YgbP protein (2.1 mg/ml), 200 µl of YchB protein (0.3 mg/ml) and 100 U of pyruvate kinase (from rabbit muscle, Type VII, E. C. 2.7.1.40, Sigma) are added. The final volume is 5 ml. The reaction mixture is incubated at 37° C. for 4 h. The reaction is monitored as described in reference example 13.

4-diphosphocytidyl-methyl-D-erythritol 2-phosphate is purified by HPLC on a column of the anionic exchanger Nucleosil 5 SB (7.5×150 mm) using a gradient of 1 M amonium formiate (B) and 100 mM ammonium formiate (A) as eluent at a flow rate of 3.1 ml/min.

| t(min) | A(%) | B(%) |
|---|---|---|
| 0 | 100 | 0 |
| 5 | 100 | 0 |
| 35 | 30 | 70 |
| 40 | 30 | 70 |

The eluent is monitored by a UV-detector (Knauer) at 275 nm. 4-diphosphocytidyl-methyl-D-erythritol 2-phosphate is eluted at 26–27 min.

EXAMPLE 1

Construction of an Expression Vector and Production of an Expression Clone for the gcpE gene of *Escherichia coli*

Cells of *Escherichia coli* XL1-Blue (Bullock et al. Bio-Techniques 5, 376–379 (1987); commercial source: Stratagene, LaJolla, Calif., U.S.A.) harboring the vector pNCO113 (German patent application 19948887.8), are grown overnight in Luria Bertani (LB) medium containing 180 mg/l of ampicillin for maintenance of the plasmid in the host cells. 7 ml of the culture are centrifuged for 20 min at 5,000 rpm. The cell pellet is used for isolation of the plasmid pNCO113 with the mini plasmid isolation kit from Qiagen. The pellet is resuspended in 0.3 ml of 10 mM EDTA in 50 mM tris hydrochloride, pH 8.0. 30 µg RNase A are added. 0.3 ml of 1% (w/v) SDS in 200 mM sodium hydroxide are added and incubated for 5 min at room temperature. 0.3 ml of chilled 3.0 M sodium acetate, pH 5.5 are added and incubated for 10 min on ice. The mixture is centrifuged for 15 min at 14,000 rpm in a minifuge. The supernatant is applied onto a Qiagen-tip 20, which is previously equilibrated with 1 ml of 750 mM NaCl, 15% (v/v) ethanol and 0.15% (v/v) Triton X-100 in 50 mM MOPS, pH 7.0. The Qiagen-tip is washed four times with 1 ml of of 1000 mM NaCl and 15% (v/v) ethanol in 50 mM MOPS, pH 7.0. The DNA is eluted with 0.8 ml of 1250 mM NaCl and 15% (v/v) ethanol in 50 mM tris hydrochloride, pH 8.5. The DNA is precipitated with 0.56 ml of isopropanol, centrifuged 30 min at 14,000 rpm and washed with 1 ml of ice-cold 70% (v/v) ethanol. After drying in a speedvac for 5 min, the DNA is dissolved in 50 µl of redistilled $H_2O$. The solution contains 7 µg of the vector DNA pNCO113.

The *E. coli* ORF gcpE (accession no. gb AE000338) is amplified from base pair (bp) position 372 to 1204 by PCR using chromosomal *E. coli* DNA as template. The reaction mixture contains 25 pmol of the primer 5'-GAGGAGAAAT-TAACCATGCATAACCAGGCTCC-3', 25 pmol of the primer 5'-CGAGGCGGATCCCATCACG-3', 20 ng of chromosomal DNA, 2 U of Taq DNA polymerase (Eurogentec, Seraing, Belgium) and 20 nmol of dNTPs in a total volume of 100 µl of 1.5 mM $MgCl_2$, 50 mM KCl, 10 mM tris hydrochloride, pH 8.8 and 0.1% (w/w) Triton X-100.

The mixture is denaturated for 3 min at 95° C. Then 30 PCR cycles for 45 sec at 94° C., 45 sec at 50° C. and 60 sec at 72° C. follow. After further incubation for 7 min at 72° C., the mixture is cooled to 4° C. An aliquot of 2 µl is subjected to agarose gel electrophoresis.

The PCR amplificate is purified with the PCR purification kit from Qiagen (Hilden, Germany). To 100 µl of PCR reaction mixture 300 µl of QX1 buffer are added and the mixture is applied to a Qiaquick spin column and centrifuged for 1 min at 14,000 rpm. The flow through is discarded. 0.75 ml of buffer PE (Qiagen) are loaded on the column and centrifuged as before. The flow through is discarded and the column is centrifuged for an additional 1 min at 14,000 rpm. The column is placed in a clean 1.5 ml eppendorf tube. 50 µl of $H_2O$ (redistilled, sterile) are added to the column and it is centrifuged for 1 min at 14,000 rpm. The flow through contains 1.2 µg of purified PCR product.

The PCR amplificate is used as template for a second PCR reaction. The reaction mixture contains 25 pmol of the primer 5'-ACACAGAATTCATTAAAGAGGAGAAAT-TAACCATG-3', 25 pmol of the primer 5'-CGAGGCG-GATCCCATCACG-3', 2 µl of the first PCR amplification, 2 U of Taq DNA polymerase (Eurogentec, Seraing, Belgium) and 20 nmol of dNTPs in a total volume of 100 µl containing 1.5 mM $MgCl_2$, 50 mM KCl, 10 mM tris hydrochloride, pH 8.8 and 0.1% (w/w) Triton X-100.

The mixture is denaturated for 3 min at 95° C. Then 30 PCR cycles for 45 sec at 94° C., 45 sec at 50° C. and 60 sec at 72° C. follow. After further incubation for 7 min at 72° C., the mixture is cooled to 4° C. An aliquot of 2 µl is subjected to agarose gel electrophoresis.

The PCR amplificate is purified with the PCR purification kit from Qiagen as described above. 1.1 µg of purified PCR product are obtained. 2.0 µg of the vector pNCO113 and 1.1 µg of the purified PCR product are digested in order to produce DNA fragments with overlapping ends. Each restriction mixture contains 5 µl of NEB3 buffer from New England Biolabs (NEB, Schwalbach, Germany), 20 U of EcoRI (NEB), BamHI (NEB), in a total volume of 50 µl and is incubated for 3 h at 37° C. Digested vector DNA and PCR product are purified using the PCR purification kit from Qiagen.

20 ng of vector DNA and 8 ng of PCR product are ligated together with 1 U of T4-Ligase (Gibco), 2 µl of T4Ligase buffer (Gibco) in a total volume of 10 µl, yielding the plasmid pNCOgcpE. The ligation mixture is incubated overnight at 4° C.

With 2 µl of the ligation mixture electrocompetent *E. coli* XL1-Blue cells are transformed.

Electrocompetent cells are prepared according to reference example 1.

Electro-transformation is done according to the description in reference example 1.

The plasmid pNCOgcpE is transformed into electrocompetent *E. coli* M15 (pREP4) (Zamenhof et al. J. Bacteriol. 110, 171–178 (1972)) cells as described above yielding the recombinant strain M15-pNCOgcpE.

The DNA sequence of the plasmid pNCOgcpE is sequenced as described in reference example 1. The DNA sequence is found to be identical with the sequence in the database (gb AE000338).

EXAMPLE 2

Construction of an Expression Vector and Production of an Expression Clone for the lytB Gene of *Escherichia coli*

The expression vector pQE30 (Qiagen) is isolated as described in reference example 1. The *E. coli* ORF lytB (accession no. gb AE000113) from basepair (bp) position 5618 to 6565 is amplified by PCR using chromosomal *E. coli* DNA as template. The reaction mixture contains 25 pmol of the primer 5'-TGGAGGGGATCCATGCAGATC-CTGTTGGCC-3', 25 pmol of primer 5'-GCATTTCTGCA-GAACTTAGGC-3', 20 ng of chromosomal DNA, 2 U of Taq DNA polymerase (Eurogentec, Seraing, Belgium) and 20 nmol of dNTPs in a total volume of 100 µl of 1.5 mM $MgCl_2$, 50 mM KCl, 10 mM tris hydrochloride, pH 8.8 and 0.1% (w/w) Triton X-100.

The mixture is denaturated for 3 min at 95° C. Then 30 PCR cycles for 60 sec at 94° C., 60 sec at 50° C. and 60 sec at 72° C. follow. After further incubation for 7 min at 72° C., the mixture is cooled to 4° C. An aliquot of 2 µl is subjected to agarose gel electrophoresis. The PCR amplificate is purified with the PCR purification kit from Qiagen as described in reference example 2. 1.9 µg of purified PCR product are obtained.

2.0 µg of the vector pQE30 and 1.5 µg of the purified PCR product are digested in order to produce DNA fragments with overlapping ends. Each restriction mixture contains 5 µl of NEB3 buffer from NEB, 20 U of BamHI (NEB), 20 U of PstI (NEB) in a total volume of 50 µl and is incubated for 3 h at 37° C. Digested vector DNA and PCR product are purified using the PCR purification kit from Qiagen.

18 ng of vector DNA and 10 ng of PCR product are ligated together with 1 U of T4-Ligase (Gibco), 2 µl of T4-Ligase buffer (Gibco) in a total volume of 10 µl, yielding the plasmid pQElytB. The ligation mixture is incubated overnight at 4° C. 2 µl of the ligation mixture is transformed into electrocompetent *E. coli* XL1-Blue cells as described in reference example 1. The electrocompetent cells are prepared as described in reference example 1.

The plasmid pQElytB M15 (pREP4) cells yield the recombinant strain M15-pQElytB. The DNA insert of the vector pQElytB is sequenced as described in reference example 1. The DNA sequence is found to be identical with the sequence in the database (gb AE000113).

EXAMPLE 3

Preparation and Purification of the Recombinant 6xHis-LytB Fusion Protein of *E. coli*

0.5 liter of Luria Bertani (LB) medium containing 90 mg of ampicillin and 25 mg kanamycin are inoculated with 10 ml of an overnight culture of *E. coli* strain M15 (pREP4) harboring plasmid pQElytB. The culture is grown in a shaking culture at 37° C. At an optical density (600 nm) of 0.7, the culture is induced with 2 mM IPTG. The culture is grown for further 5 h. The cells are harvested by centrifugation for 20 min at 5,000 rpm and 4° C. The cells are washed with 50 mM tris hydrochloride pH 8.0, centrifuged as above and frozen at −20° C. for storage.

The cells are thawed in 20 ml of 20 mM imidazole in 100 mM tris hydrochloride pH 8.0 and 0.5 M sodium chloride (standard buffer) in the presence of 1 mg/ml lysozyme and 100 µg/ml DnaseI. The mixture is incubated at 37° C. for 30 min, cooled on ice and sonified 6×10 sec with a Branson Sonifier 250 (Branson SONIC Power Company) set to 70% duty cycle output, control value of 4 output. The suspension is centrifuged at 15,000 rpm at 4° C. for 30 min. The cell free extract of recombinant LytB protein is applied on a column of $Ni^{2+}$-Chelating sepharose FF (size 2.6×6 cm, Amersham Pharmacia Biotech) previously equilibrated with 20 mM imidazole in standard buffer. The column is washed with 100 ml of starting buffer. LytB protein is eluted with a linear gradient of 20–500 mM imidazole in 100 ml of standard buffer. LytB protein containing fractions are combined according to SDS-PAGE and dialysed overnight against 100 mM tris hydrochloride pH 8.0, 5 mM dithioerythritol, 0.02% sodium azide. The homogeneity of the dialysed LytB protein is judged by SDS-PAGE. The objected band at 34 kDa is in agreement with the calculated molecular mass. 3 mg of pure enzyme were obtained.

EXAMPLE 4

Construction of an Expression Vector and Production of an Expression Clone for the yjeE Gene of *Escherichia coli*

The expression vector pNCO113 is isolated as described in reference example 1.

The *E. coli* ORF yjeE (accession no. gb AE000489) is amplified from base pair (bp) position 3299 to 3760 by PCR using chromosomal *E. coli* DNA as template. The reaction mixture contains 25 pmol of the primer 5'-GAGGAGAAAT-TAACCATGATGAATCGAGTAATTCC-3', 25 pmol of the primer 5'-GCGATACTGCAGCCCGCC-3', 20 ng of chromosomal DNA, 2 U of Taq DNA polymerase (Eurogentec, Seraing, Belgium) and 20 nmol of dNTPs in a total volume of 100 µl of 1.5 mM $MgCl_2$, 50 mM KCl, 10 mM tris hydrochloride, pH 8.8 and 0.1% (w/w) Triton X-100.

The mixture is denaturated for 3 min at 95° C. Then 30 PCR cycles for 30 sec at 94° C., 30 sec at 50° C. and 45 sec at 72° C. follow. After further incubation for 7 min at 72° C., the mixture is cooled to 4° C. An aliquot of 2 µl is subjected to agarose gel electrophoresis.

The PCR amplificate is purified with the PCR purification kit from Qiagen as described in reference example 2. 1.1 µg of purified PCR product are obtained.

The PCR amplificate is used as template for a second PCR reaction. The reaction mixture contains 25 pmol of the primer 5'-ACACAGAATTCATTAAAGAGGAGAAAT-TAACCATG-3', 25 pmol of the primer 5'-GCGATACTG-CAGCCCGCC-3', 2 µl of the first PCR amplification, 2 U of Taq DNA polymerase (Eurogentec, Seraing, Belgium) and 20 nmol of dNTPs in a total volume of 100 µl containing 1.5 mM $MgCl_2$, 50 mM KCl, 10 mM tris hydrochloride, pH 8.8 and 0.1% (w/w) Triton X-100.

The mixture is denaturated for 3 min at 95° C. Then 30 PCR cycles for 30 sec at 94° C., 30 sec at 50° C. and 45 sec at 72° C. follow. After further incubation for 7 min at 72° C., the mixture is cooled to 4° C. An aliquot of 2 µl is subjected to agarose gel electrophoresis.

The PCR amplificate is purified with PCR purification kit from Qiagen as described above. 1.0 µg of purified PCR product are obtained. 2.0 µg of the vector pNCO113 and 1.1 µg of the purified PCR product are digested in order to produce DNA fragments with overlapping ends. Each restriction mixture contains 5 µl of NEB3 buffer from NEB, 20 U of EcoRI (NEB), PstI (NEB), in a total volume of 50 µl and is incubated for 3 h at 37° C. Digested vector DNA and PCR product are purified using the PCR purification kit from Qiagen.

20 ng of vector DNA and 8 ng of PCR product are ligated together with 1 U of T4-Ligase (Gibco), 2 µl of T4-Ligase buffer (Gibco) in a total volume of 10 μl yielding the plasmid pNCOyjeE. The ligation mixture is incubated overnight at 4° C.

2 μl of the ligation mixture is transformed into electrocompetent *E. coli* XL1-Blue as described in reference example 1 yielding the recombinant strain XL1-pNCOyjeE.

The DNA sequence of the plasmid pNCOyjeE is sequenced as described in reference example 1. The DNA sequence is found to be identical with the sequence in the database (gb AE000489).

EXAMPLE 5

Construction of an Expression Vector and Production of an Expression Clone for the ybeB Gene of *Escherichia coli*

The expression vector pQE30 is isolated as described in reference example 1.

The *E. coli* ORF ybeB (gb AE000168) is amplified from base pair (bp) position 6454 to 6663 by PCR using chromosomal *E. coli* DNA as template. The reaction mixture contains 25 pmol of the primer 5'-CCAGGGGGGATCCAT-GCAGGGTAAAGC-3', 25 pmol of the primer 5'-GTTG-CAGCTGCAGGCATTAACTCC-3', 20 ng of chromosomal DNA, 2 U of Taq DNA polymerase (Eurogentec, Seraing, Belgium) and 20 nmol of dNTPs in a total volume of 100 μl of 1.5 mM $MgCl_2$, 50 mM KCl, 10 mM tris hydrochloride, pH 8.8 and 0.1% (w/w) Triton X-100.

The mixture is denaturated for 3 min at 95° C. Then 30 PCR cycles for 30 sec at 94° C., 30 sec at 50° C. and 45 sec at 72° C. follow. After further incubation for 7 min at 72° C., the mixture is cooled to 4° C. An aliquot of 2 μl is subjected to agarose gel electrophoresis.

The PCR amplificate is purified with the PCR purification kit from Qiagen as described in reference example 2. 1.5 μg of purified PCR product are obtained. 2.0 μg of the vector pQE30 and 1.0 μg of the purified PCR product are digested in order to produce DNA fragments with overlapping ends. Each restriction mixture contains 5 μl of NEB3 buffer from NEB, 20 U of BamHI (NEB) and PstI (NEB), in a total volume of 50 μl and is incubated for 3 h at 37° C. Digested vector DNA and PCR product are purified using the PCR purification kit from Qiagen.

20 ng of vector DNA and 6 ng of PCR product are ligated together with 1 U of T4-Ligase (Gibco), 2 μl of T4-Ligase buffer (Gibco) in a total volume of 10 μl yielding the plasmid pNCOyjeE. The ligation mixture is incubated overnight at 4° C.

2 μl of the ligation mixture is transformed into electrocompetent *E. coli* XL1-Blue as described in reference example 1 yielding the recominant strain XL1-pQE30ybeB.

The DNA sequence of the plasmid pQEybeB is sequenced as described in reference example 1. The DNA sequence is found to be identical with the sequence in the database (gb AE000168).

EXAMPLE 6

Consumption Assay of 2C-methyl-D-erythritol 2,4-cyclopyrophosphate Using Protein Fraction of *E. coli*

Assay mixtures for direct detection of enzymatic products formed from 2C-methyl-D-erythritol 2,4-cyclopyrophosphate via reversed-phase ion-pair HPLC contain 100 mM tris hydrochloride pH 8.0, 10 mM $MgCl_2$, 25 μM of [$2-^{14}C$]-2C-methyl-D-erythritol 2,4-cyclopyrophosphate (15.8 μCi/μMol) and protein in a total volume of 200 μl. They are incubated at 37° C. for 4 hours. The reactions are stopped by freezing the samples in liquid nitrogen and the reaction mixtures are centrifuged. Aliquots (50 μl) of the supernatant are applied to a Multospher 120 RP 18 column (5 μm, crystalline silica gel, 4.6×250 mm, CS-Chromatographie Service GmbH, Langerwehe, Germany) which has been equilibrated with 10 mM tetra-n-butylammonium hydrogensulfate pH 6.0 at a flow rate of 0.75 ml/min. The column is developed with 15 ml of 10 mM tetra-n-butylammonium hydrogensulfate pH 6.0 and further by a linear gradient of 0 to 42% (v/v) methanol in 45 ml of 10 mM tetra-n-butylammonium hydrogen sulfate pH 6.0. The effluent is monitored using a radiodetector (Beta-RAM, Biostep GmbH, Jahnsdorf, Germany). The retention volumes of 2C-methyl-D-erythritol 2,4-cyclopyrophosphate, a new product and isopentenyl pyrophosphate are 31.5, 40 and 59 ml respectively. This assay can be carried out in the presence or absence of prospective inhibitors by measuring the residual amount of starting material or the amount of product and comparing the results.

EXAMPLE 7

Assays with Chromoplasts of *Narcissus pseudonarcissus*

Chromoplasts of *Narcissus pseudonarcissus* are prepared according to a method described by Kleinig and Beyer (in: Methods in Enzymology (Law, J. H. and Rilling, H. C., eds) 110, 267–273 (1985), Academic Press, London).

Assay mixtures contain 100 mM Hepes pH 7.6, 2 mM $MnCl_2$, 10 mM $MgCl_2$, 2 mM $NADP^+$, 20 μM FAD, 5 mM NaF, 6 mM ATP, 1 mM NADPH, 64 μM [$2-^{14}C$]-2C-methyl-D-erythritol 2,4-cyclopyrophosphate (15.8 μCi/μMol) and 1 mg chromoplasts in a total volume of 500 μl. The mixture is incubated at 30° C. for 240 min and analyzed by HPLC on the occurence of new metabolites by as decribed in example 6. Peaks of new metabolites with retention volumes of 40, 47 and 59 ml are obtained.

EXAMPLE 8

Enzymatic Preparation of a New Metabolite of the Non-Mevalonate Pathway 25 g of M15 (pREP4) cells grown overnight in M9 minimal medium (Sambrook et al., Molecular Cloning, 2nd edition (1989), Cold Spring Harbor Press) are harvested by centrifugation and resuspended in 150 ml of a solution of 10 mM $MgCl_2$, 5 mM dithiothreitol and 100 mM tris hydrochloride pH 8.0. 100 mg of lysozyme are added and the reaction mixture is incubated for 30 min at 37° C. The mixture is cooled on ice and sonified 6×10 sec with a Branson Sonifier 250 (Branson SONIC Power Company) set to 70% duty cycle output, control value of 4 output and centrifuged for 60 min at 10,000 rpm. The pellet is resuspended in 200 ml of 100 mM tris hydrochloride, pH 8.0, 5 mM $CoCl_2$, 10 mM $MgCl_2$, 5 mM dithiothreitol and 27.3 μM [$U-^{13}C_5$, $2-^{14}C$]-2C-methyl-D-erythritol 2,4-cyclopyrophosphate (0.72 μCi/μMol) are added and the mixture is incubated for 8 h at 37° C. The mixture is centrifuged at 10,000 rpm for 60 min and the supernatant is lyophilized. The dried substance is dissolved in 20 ml destined water. An aliquot of 100 μl is analyzed by HPLC on the occurence of a new product peak at 40 min as described in example 6. 150 ml ethanol are added and the mixture is centrifuged at 4,800 rpm for 30 min. The pellet is resuspended in 130 ml ethanol, 100 mg barium acetate are added to the suspension and the suspension is kept overnight at 4° C. The mixture is centrifuged at 4,800 rpm for 30 min and the pellet is collected by centrifugation at 4,800 rpm for 30 min. The pellet is resuspended in 5 ml destined water and beads of a cation exchanger (AG-50W-x8, sodium form, Biorad, München) are added until a clear solution is obtained. The solution is passed through a filter of Whatman paper and the filtrate is lyophilized. The dried substance is dissolved in 0.5 ml of $D_2O$.

---

The invention claimed is:

1. A method for screening chemical libraries for the presence or absence of inhibition of the biosynthesis of isoprenoids by blocking the biosynthetic conversion of 2C-methyl-D-erythritol 2,4-cyclopyrophosphate to isopentyl pyrophosphate (IPP) or dimethylallyl pyrophosphate (DMAPP), comprising:

(a) preparing an aqueous mixture comprising intact or lysed plastids or bacterial cells, 2C-methyl-D-erythritol 2,4-cyclopyrophosphate and a divalent metal salt;

(b) reacting said mixture for a predetermined period of time at a predetermined temperature;

(c) detecting the amount of conversion of 2C-methyl-D-erythritol 2,4-cyclopyrophosphate to IPP or DMAPP by measuring the amount of consumption of 2C-methyl-D-erythritol 2,4-cyclopyrophosphate;

(d) repeating steps (a) to (c) in the presence of a test sample of a chemical library; and (e) determining the presence or absence of inhibition in step (d) by ascertaining whether or not the detected amount of conversion of 2C-methyl-D-erythsitol 2,4-cyclopyrophosphate to IPP to DMAPP is lower in the presence of the test sample.

2. The method according to claim 1, wherein the divalent metal salt is at least one selected from the group of cobalt salt, magnesium salt and manganese salt.

3. A method for screening chemical libraries for the presence or absence of inhibition of the biosynthesis of isoprenoids by blocking the biosynthetic conversion of 2C-methyl-D-erythritol 2,4-cyclopyrophosphate to isopentyl pyrophosphate (IPP) or dimethylallyl pyrophosphate (DMAPP), comprising:

(a) preparing an aqueous mixture comprising intact or lysed plastids or bacterial cells, 2C-methyl-D-erythritol 2,4-cyclopyrophosphate and a divalent metal salt;

(b) reacting said mixture for a predetermined period of time at a predetermined temperature;

(c) detecting the amount of conversion of 2C-methyl-D-erythritol 2,4-cyclopyrophosphate to IPP or DMAPP by measuring the amount of formation of an intermediate that has a retention volume of 1.27±0.15 times that of 2C-methyl-D-erythritol 2,4-cyclopyrophosphate and 0.68±0.06 times that of IPP when measured by reversed-phase, ion pair, high performance liquid chromatography using a 4.6×250 mm $C_{18}$ reversed-phase column (crystalline silica gel of particle size 5 µm, average pore size 12nm), equilibrated with aqueous 10mM tetra-n-butylammonium hydrogen sulfate pH 6.0 and developed with 10 mM tetra-n-butylammonium hydrogen sulfate pH 6.0 and a linear gradient of 0 to 42% (v/v) methanol in 10 mM tetra-n-butyl ammonium hydrogen sulfate at pH 6.0 and ambient temperature; (d) repeating steps (a) to (c) in the presence of a test sample of a chemical library; and (e) determining the presence or absence of inhibition in step (d) by ascertaining whether or not the detected amount of conversion of 2C-methyl-D-erythritol 2,4-cyclopyrophosphate to IPP or DMAPP is lower in the presence of the test sample.

4. The method according to claim 3, wherein the divalent metal salt is at least one selected from the group of cobalt salt, magnesium salt and manganese salt.

5. A method for screening chemical libraries for the presence or absence of inhibition of the biosynthesis of isoprenoids by blocking the biosynthetic conversion of 2C-methyl-D-erythritol 2,4-cyclopyrophosphate to isopentyl pyrophosphate (IPP) or dimethylallyl pyrophosphate (DMAPP), comprising:

(a) preparing an aqueous mixture comprising intact or lysed plastids or bacterial cells, 2C-methyl-D-erythritol 2,4-cyclopyrophosphate and a divalent metal salt;

(b) reacting said mixture for a predetermined period of time at a predetermined temperature;

(c) detecting the amount of conversion of 2C-methyl-D-erythritol 2,4-cyclopyrophosphate to IPP or DMAPP by measuring the amount of formation of IPP or DMAPP;

(d) repeating steps (a) to (c) in the presence of a test sample of a chemical library; and (e) determining the presence or absence of inhibition in step (d) by ascertaining whether or not the detected amount of conversion of 2C-methyl-D-erythritol 2,4-cyclopyrophosphate to IPP or DMAPP is lower in the presence of the test sample.

6. The method according to claim 5, wherein the divalent metal salt is at least one selected from the group of cobalt salt, magnesium salt and manganese salt.

* * * * *

UNITED STATES PATENT AND TRADEMARK OFFICE
CERTIFICATE OF CORRECTION

PATENT NO. : 7,288,367 B2
APPLICATION NO. : 10/296416
DATED : October 30, 2007
INVENTOR(S) : Bacher et al.

It is certified that error appears in the above-identified patent and that said Letters Patent is hereby corrected as shown below:

On Title Page:

Item (30) Foreign Application Priority Data: Should read

--Jun. 5, 2000 (DE) 100 27 821.3--

Column 47:

Claim 1, Line 65: Please correct "2C-methyl-D-erythsitol"
To read --2C-methyl-D-erythritol--

Signed and Sealed this

Eighth Day of April, 2008

JON W. DUDAS
*Director of the United States Patent and Trademark Office*

SEQUENCE LISTING

<160> NUMBER OF SEQ ID NOS: 23

<210> SEQ ID NO 1
<211> LENGTH: 59
<212> TYPE: DNA
<213> ORGANISM: Artificial sequence
<220> FEATURE:
<223> OTHER INFORMATION: DNA linker

<400> SEQUENCE: 1
cacacagaat tcattaaaga ggagaaatta accatgggag gatccgtcga cctgcagcc      59

<210> SEQ ID NO 2
<211> LENGTH: 59
<212> TYPE: DNA
<213> ORGANISM: Artificial Sequence
<220> FEATURE:
<223> OTHER INFORMATION: DNA linker

<400> SEQUENCE: 2
ggctgcaggt cgacggatcc tcccatggtt aatttctcct ctttaatgaa ttctgtgtg      59

<210> SEQ ID NO 3
<211> LENGTH: 31
<212> TYPE: DNA
<213> ORGANISM: Artificial sequence
<220> FEATURE:
<223> OTHER INFORMATION: Primer

<400> SEQUENCE: 3
tgatccgcca tggatctttt atcaatacag g                                   31

<210> SEQ ID NO 4
<211> LENGTH: 20
<212> TYPE: DNA
<213> ORGANISM: Artificial sequence
<220> FEATURE:
<223> OTHER INFORMATION: Primer

<400> SEQUENCE: 4
ttgaatagag gatccccgcc                                                20

<210> SEQ ID NO 5
<211> LENGTH: 24
<212> TYPE: DNA
<213> ORGANISM: Artificial sequence
<220> FEATURE:
<223> OTHER INFORMATION: Primer

<400> SEQUENCE: 5
ggaggatcca tgaagcaact cacc                                           24

<210> SEQ ID NO 6
<211> LENGTH: 20
<212> TYPE: DNA
<213> ORGANISM: Artificial sequence
<220> FEATURE:
<223> OTHER INFORMATION: Primer

<400> SEQUENCE: 6

-continued gcgcgactct ctgcagccgg                                        20

<210> SEQ ID NO 7
<211> LENGTH: 28
<212> TYPE: DNA
<213> ORGANISM: Artificial sequence
<220> FEATURE:
<223> OTHER INFORMATION: Primer

<400> SEQUENCE: 7
aaattaacca tggcaaccac tcatttgg                               28

<210> SEQ ID NO 8
<211> LENGTH: 21
<212> TYPE: DNA
<213> ORGANISM: Artificial sequence
<220> FEATURE:
<223> OTHER INFORMATION: Primer

<400> SEQUENCE: 8
ttgggcctgc agcgccaaag g                                      21

<210> SEQ ID NO 9
<211> LENGTH: 32
<212> TYPE: DNA
<213> ORGANISM: Artificial sequence
<220> FEATURE:
<223> OTHER INFORMATION: Primer

<400> SEQUENCE: 9
gaggagaaat taaccatgcg gacacagtgg cc                          32

<210> SEQ ID NO 10
<211> LENGTH: 23
<212> TYPE: DNA
<213> ORGANISM: Artificial sequence
<220> FEATURE:
<223> OTHER INFORMATION: Primer

<400> SEQUENCE: 10
gtcaccgaac tgcagcttgc ccg                                    23

<210> SEQ ID NO 11
<211> LENGTH: 35
<212> TYPE: DNA
<213> ORGANISM: Artificial sequence
<220> FEATURE:
<223> OTHER INFORMATION: Primer

<400> SEQUENCE: 11
acacagaatt cattaaagag gagaaattaa ccatg                       35

<210> SEQ ID NO 12
<211> LENGTH: 23
<212> TYPE: DNA
<213> ORGANISM: Artificial sequence
<220> FEATURE:
<223> OTHER INFORMATION: Primer

<400> SEQUENCE: 12
gtcaccgaac tgcagcttgc ccg                                    23

<210> SEQ ID NO 13
<211> LENGTH: 37
<212> TYPE: DNA
<213> ORGANISM: Artificial sequence

```
<220> FEATURE:
<223> OTHER INFORMATION: Primer

<400> SEQUENCE: 13
gaggagaaat taaccatgcg aattggacac ggttttg                              37

<210> SEQ ID NO 14
<211> LENGTH: 33
<212> TYPE: DNA
<213> ORGANISM: Artificial sequence
<220> FEATURE:
<223> OTHER INFORMATION: Primer

<400> SEQUENCE: 14
tattatctgc agccttgcgg tttaccgtgg agg                                  33

<210> SEQ ID NO 15
<211> LENGTH: 36
<212> TYPE: DNA
<213> ORGANISM: Artificial sequence
<220> FEATURE:
<223> OTHER INFORMATION: Primer

<400> SEQUENCE: 15
gagaaggatc catgcgaatt ggacacggtt ttgacg                               36

<210> SEQ ID NO 16
<211> LENGTH: 32
<212> TYPE: DNA
<213> ORGANISM: Artificial sequence
<220> FEATURE:
<223> OTHER INFORMATION: Primer

<400> SEQUENCE: 16
gaggagaaat taaccatgca taaccaggct cc                                   32

<210> SEQ ID NO 17
<211> LENGTH: 19
<212> TYPE: DNA
<213> ORGANISM: Artificial sequence
<220> FEATURE:
<223> OTHER INFORMATION: Primer

<400> SEQUENCE: 17
cgaggcggat cccatcacg                                                  19

<210> SEQ ID NO 18
<211> LENGTH: 30
<212> TYPE: DNA
<213> ORGANISM: Artificial sequence
<220> FEATURE:
<223> OTHER INFORMATION: Primer

<400> SEQUENCE: 18
tggaggggat ccatgcagat cctgttggcc                                     30

<210> SEQ ID NO 19
<211> LENGTH: 21
<212> TYPE: DNA
<213> ORGANISM: Artificial sequence
<220> FEATURE:
<223> OTHER INFORMATION: Primer

<400> SEQUENCE: 19
gcatttctgc agaacttagg c                                              21
```

```
<210> SEQ ID NO 20
<211> LENGTH: 35
<212> TYPE: DNA
<213> ORGANISM: Artificial sequence
<220> FEATURE:
<223> OTHER INFORMATION: Primer

<400> SEQUENCE: 20
gaggagaaat taaccatgat gaatcgagta attcc                              35

<210> SEQ ID NO 21
<211> LENGTH: 18
<212> TYPE: DNA
<213> ORGANISM: Artificial sequence
<220> FEATURE:
<223> OTHER INFORMATION: Primer

<400> SEQUENCE: 21
gcgatactgc agcccgcc                                                 18

<210> SEQ ID NO 22
<211> LENGTH: 27
<212> TYPE: DNA
<213> ORGANISM: Artificial sequence
<220> FEATURE:
<223> OTHER INFORMATION: Primer

<400> SEQUENCE: 22
ccagggggga tccatgcagg gtaaagc                                       27

<210> SEQ ID NO 23
<211> LENGTH: 24
<212> TYPE: DNA
<213> ORGANISM: Artificial sequence
<220> FEATURE:
<223> OTHER INFORMATION: Primer

<400> SEQUENCE: 23
gttgcagctg caggcattaa ctcc                                          24
```